United States Patent
Hart et al.

(10) Patent No.: US 9,445,806 B2
(45) Date of Patent: Sep. 20, 2016

(54) SUTURE HOLDER DELIVERY SYSTEM

(71) Applicant: Karl Storz GmbH & Co. KG, Tuttlingen (DE)

(72) Inventors: Rickey Hart, Marco Island, FL (US); Thore Zantop, Muenster (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 626 days.

(21) Appl. No.: 13/707,229

(22) Filed: Dec. 6, 2012

(65) Prior Publication Data

US 2013/0096613 A1 Apr. 18, 2013

Related U.S. Application Data

(63) Continuation-in-part of application No. 12/367,247, filed on Feb. 6, 2009.

(51) Int. Cl.
*A61B 17/04* (2006.01)
*A61B 17/00* (2006.01)

(52) U.S. Cl.
CPC ...... *A61B 17/0401* (2013.01); *A61B 2017/003* (2013.01); *A61B 2017/00367* (2013.01);
(Continued)

(58) Field of Classification Search
CPC .................. A61B 17/0401; A61B 2017/0409; A61B 17/0487; A61B 17/128; A61B 17/1285; A61B 2017/0488
USPC .................................. 606/139, 144–148, 232
See application file for complete search history.

(56) References Cited

U.S. PATENT DOCUMENTS

| 757,820 A | 4/1904 | Lykke |
| 3,880,166 A | 4/1975 | Fogarty |

(Continued)

FOREIGN PATENT DOCUMENTS

| JP | 2004515273 A | 5/2004 |
| WO | 0139671 A1 | 6/2001 |

(Continued)

OTHER PUBLICATIONS

ARTHREX product advertisement; "Meniscal Clinch (TM)"; www.arthrex.com; ARTHREX, Inc.; 2009 (retrieved from internet Sep. 10, 2009; web site developed Nov. 1998); 1 page.

(Continued)

*Primary Examiner* — Todd E Manahan
*Assistant Examiner* — Casey B Lewis
(74) *Attorney, Agent, or Firm* — Whitmyer IP Group LLC

(57) ABSTRACT

A suture holder delivery system including a housing having a distal end and a proximal end, a first driver mechanism and a second driver mechanism, each movable in a longitudinal direction with respect to the housing, a first delivery needle and a second delivery needle, the first delivery needle connected at a proximal end to the first driver mechanism and the second delivery needle connected at a proximal end to the second driver mechanism, the first driver mechanism and said second driver mechanism each having fully retracted and fully extended positions and a toggle assembly operable to fix at least one of the first driver mechanism and second driver mechanism in at least one longitudinal position. The delivery system may include a locking mechanism operable to prevent the second driver mechanism from being moved in a distal direction until the first driver mechanism is longitudinally advanced to the extended position.

15 Claims, 29 Drawing Sheets

(52) U.S. Cl.
CPC ...... *A61B2017/0409* (2013.01); *A61B 2017/0414* (2013.01); *A61B 2017/0417* (2013.01); *A61B 2017/0438* (2013.01); *A61B 2017/0459* (2013.01); *A61B 2017/0462* (2013.01); *A61B 2017/0464* (2013.01)

(56) References Cited

U.S. PATENT DOCUMENTS

| | | | |
|---|---|---|---|
| 4,823,794 | A | 4/1989 | Pierce |
| 5,693,060 | A | 12/1997 | Martin |
| 6,464,698 | B1 * | 10/2002 | Falwell ............ A61B 18/1492 606/41 |
| 6,635,073 | B2 | 10/2003 | Bonutti |
| 6,638,286 | B1 * | 10/2003 | Burbank ............ A61B 17/0469 606/139 |
| 6,652,561 | B1 | 11/2003 | Tran |
| 6,972,027 | B2 * | 12/2005 | Fallin ................. A61B 17/0401 606/139 |
| 7,153,312 | B1 | 12/2006 | Torrie et al. |
| 7,594,923 | B2 | 9/2009 | Fallin et al. |
| 7,722,644 | B2 | 5/2010 | Fallin et al. |
| 7,887,551 | B2 | 2/2011 | Bojarski et al. |
| 2002/0019649 | A1 | 2/2002 | Sikora et al. |
| 2003/0130694 | A1 | 7/2003 | Bojarski et al. |
| 2004/0002734 | A1 | 1/2004 | Fallin et al. |
| 2004/0153074 | A1 * | 8/2004 | Bojarski ............ A61B 17/0401 606/232 |
| 2005/0251157 | A1 | 11/2005 | Saadat et al. |
| 2005/0288709 | A1 | 12/2005 | Fallin et al. |
| 2005/0288711 | A1 | 12/2005 | Fallin et al. |
| 2007/0100348 | A1 * | 5/2007 | Cauthen, III ...... A61B 17/0401 606/99 |
| 2008/0140092 | A1 * | 6/2008 | Stone ................. A61B 17/0401 606/144 |
| 2009/0112232 | A1 * | 4/2009 | Crainich ............ A61B 17/0401 606/139 |
| 2009/0206124 | A1 * | 8/2009 | Hall .................. A61B 17/07207 227/175.1 |
| 2011/0270278 | A1 | 11/2011 | Overes et al. |
| 2012/0172924 | A1 | 7/2012 | Allen, IV |
| 2012/0184972 | A1 | 7/2012 | Lam et al. |

FOREIGN PATENT DOCUMENTS

| | | |
|---|---|---|
| WO | 0236020 A1 | 5/2002 |
| WO | 2012096706 A1 | 7/2012 |
| WO | 2012151592 A2 | 11/2012 |

OTHER PUBLICATIONS

Smith & Nephew Technique Plus Illustrated Guide(TM), Meniscal Repair with the FasT-Fix(TM) Suture System, Smith & Nephew, Inc., Andover, MA 01810 USA, Mar. 2002, 1061031 Rev. B (11 pages).

European Search Report Application No. EP 13 19 5808 Completed: Feb. 28, 2014; Mailing Date: Mar. 11, 2014 5 pages.

Partial European Search Report Application No. EP 13 19 5554 Completed: Feb. 28, 2014; Mailing Date: Mar. 11, 2014 7 pages.

European Search Report Application No. EP 13 19 5554 Completed: Jul. 14, 2014; Mailing Date: Jul. 23, 2014 13 pages.

* cited by examiner

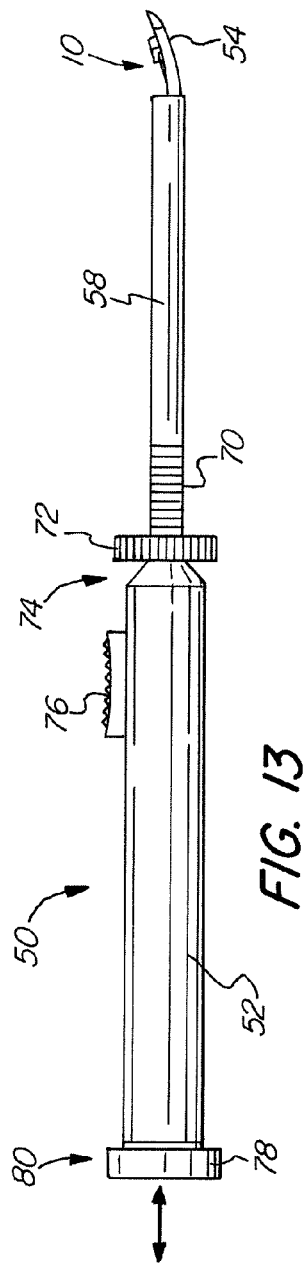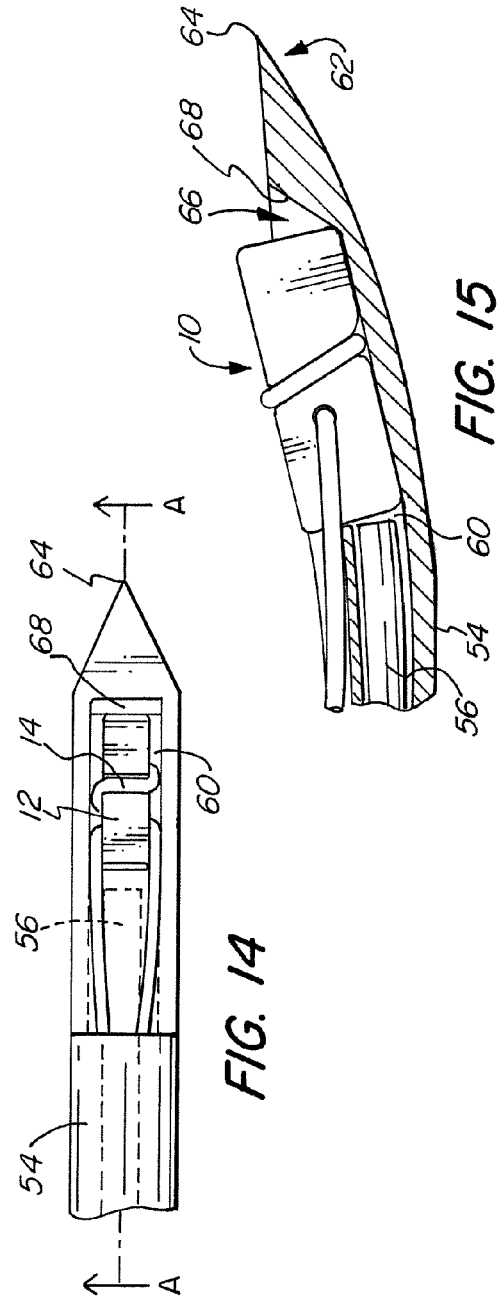
FIG. 13
FIG. 14
FIG. 15

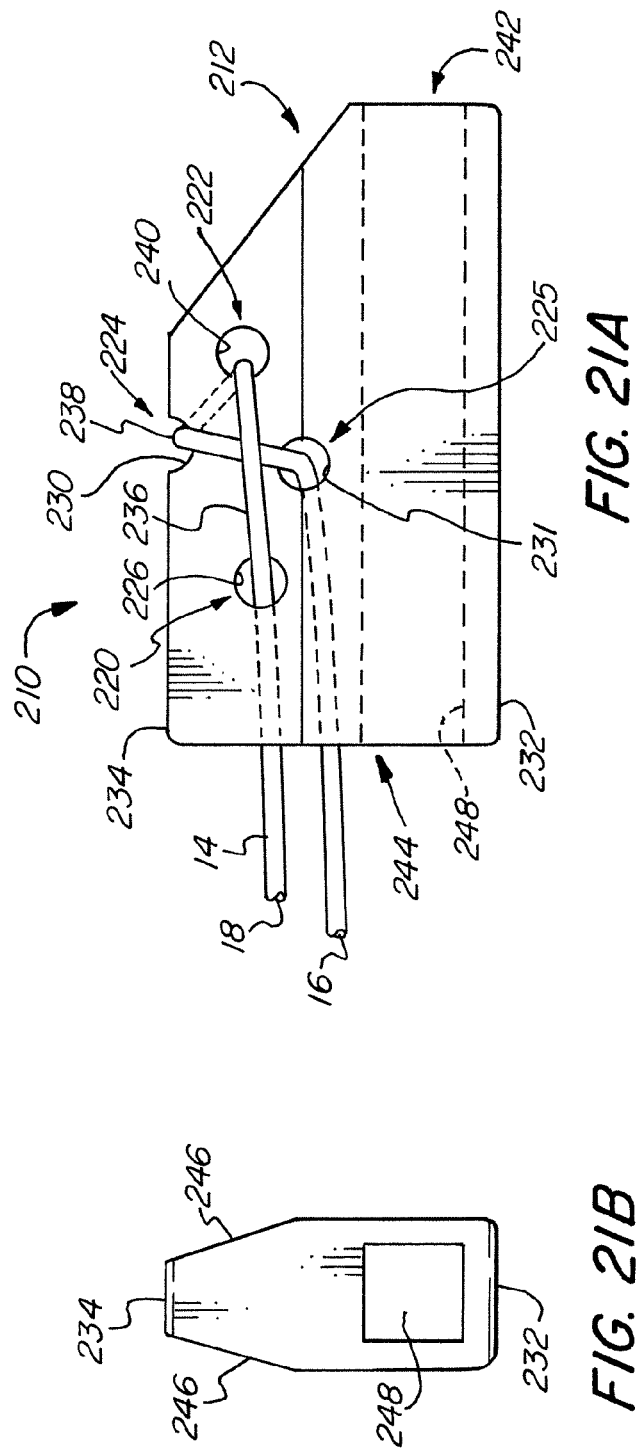

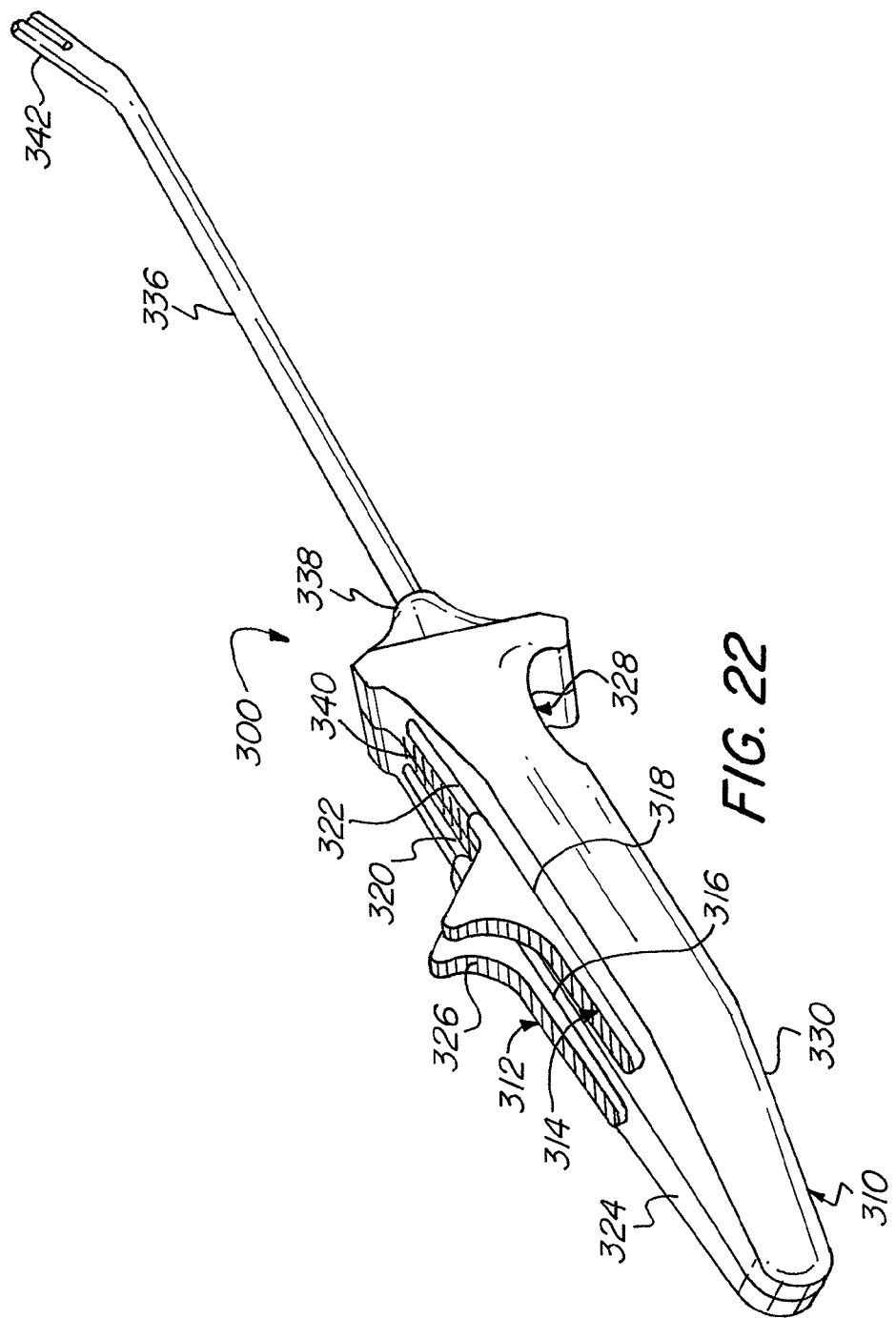

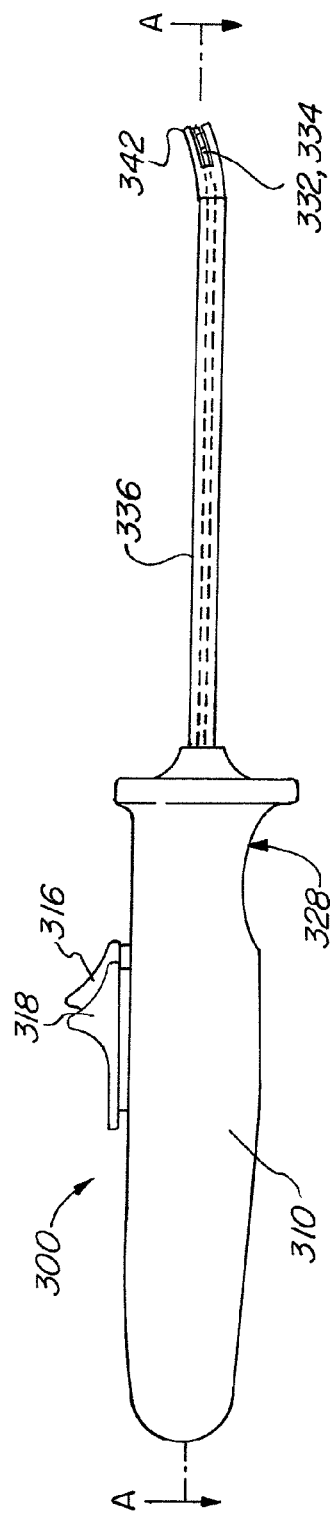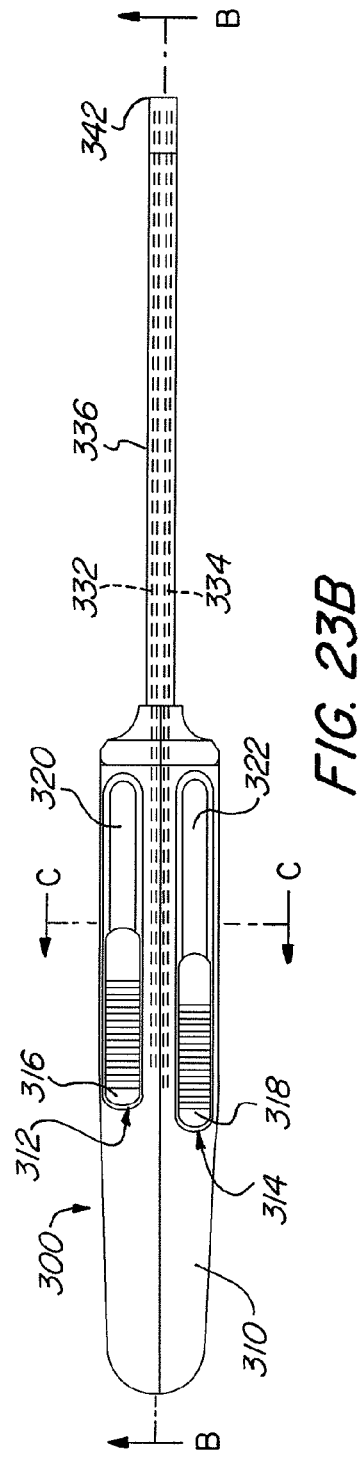
FIG. 23A
FIG. 23B

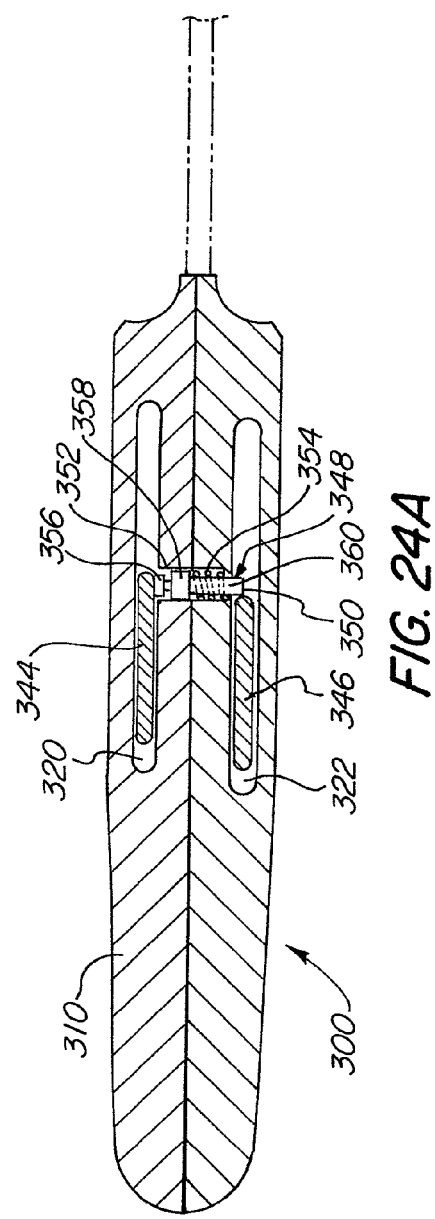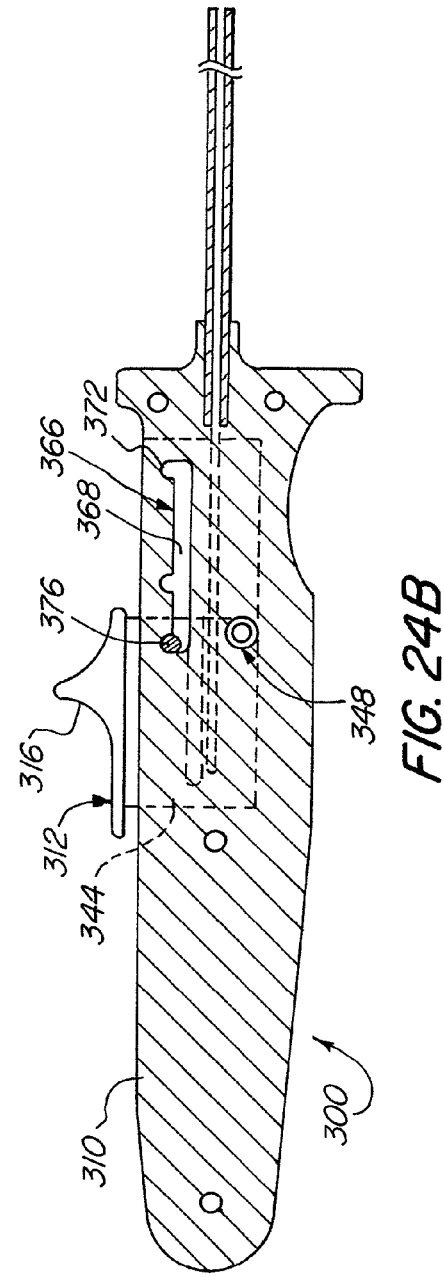

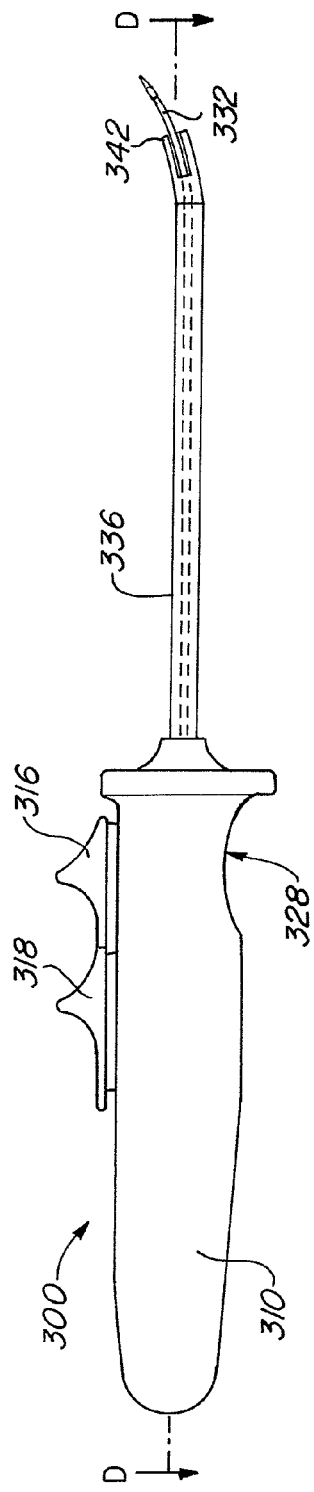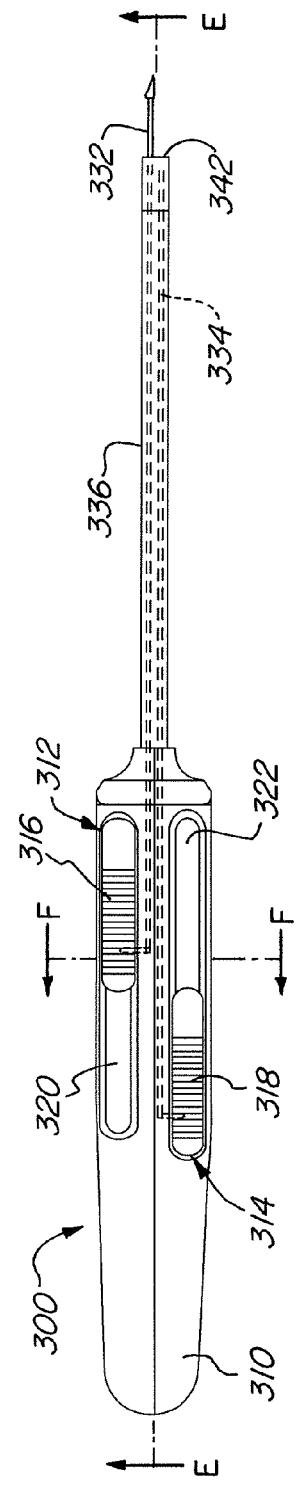

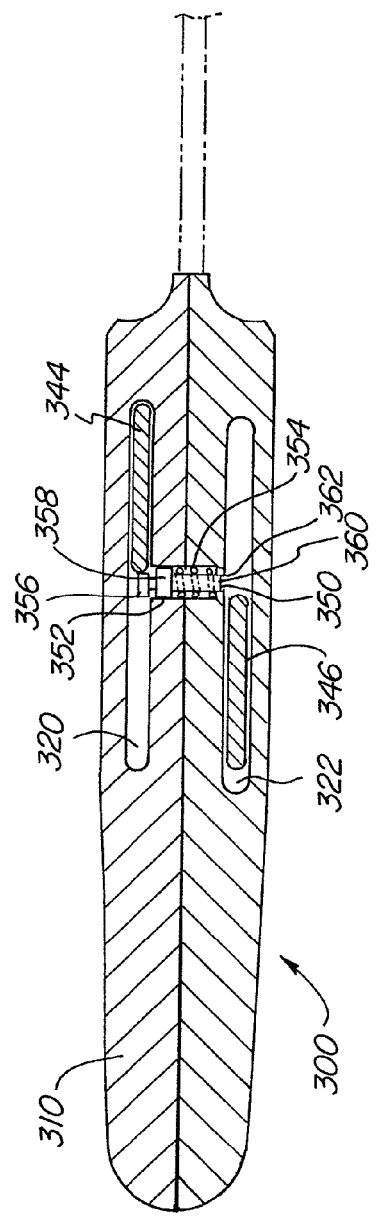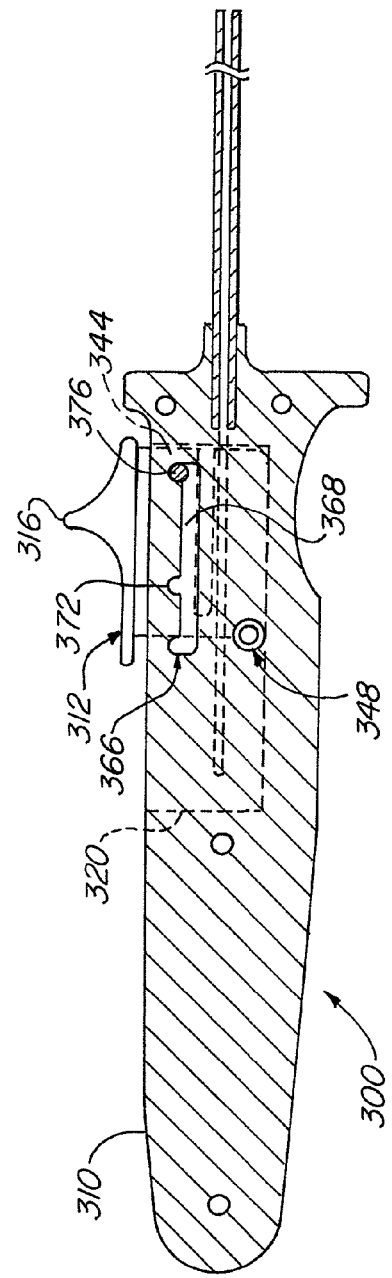
FIG. 28A
FIG. 28B

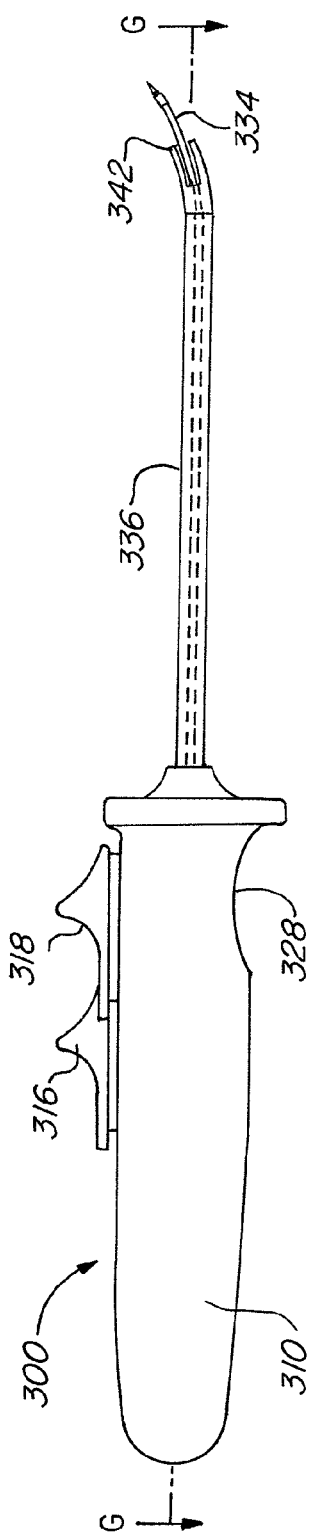
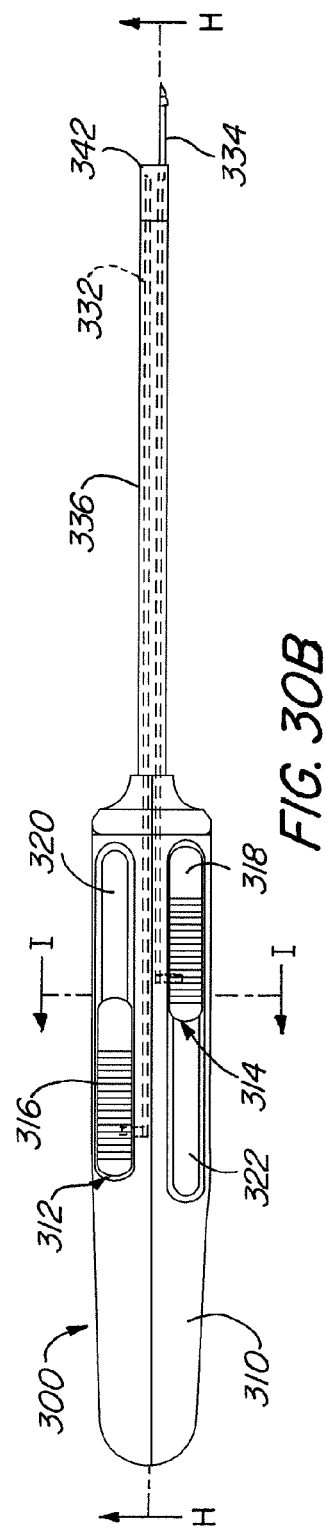
FIG. 30A
FIG. 30B

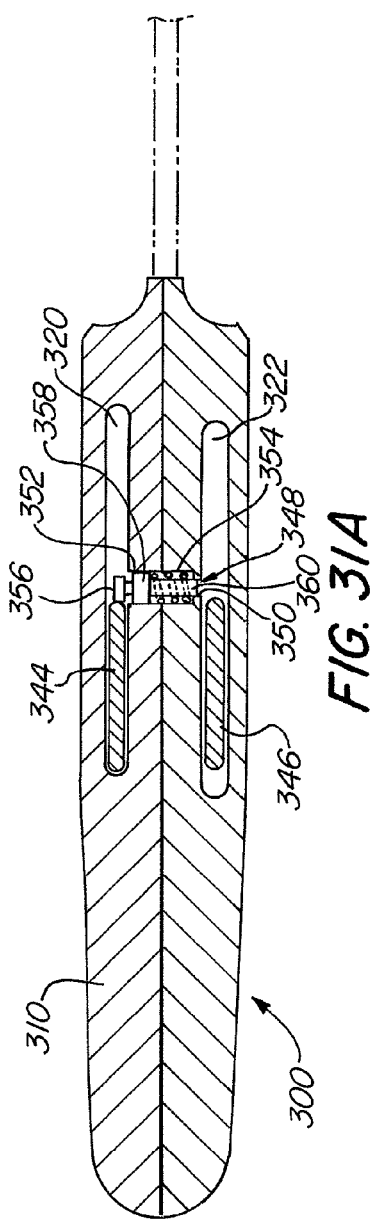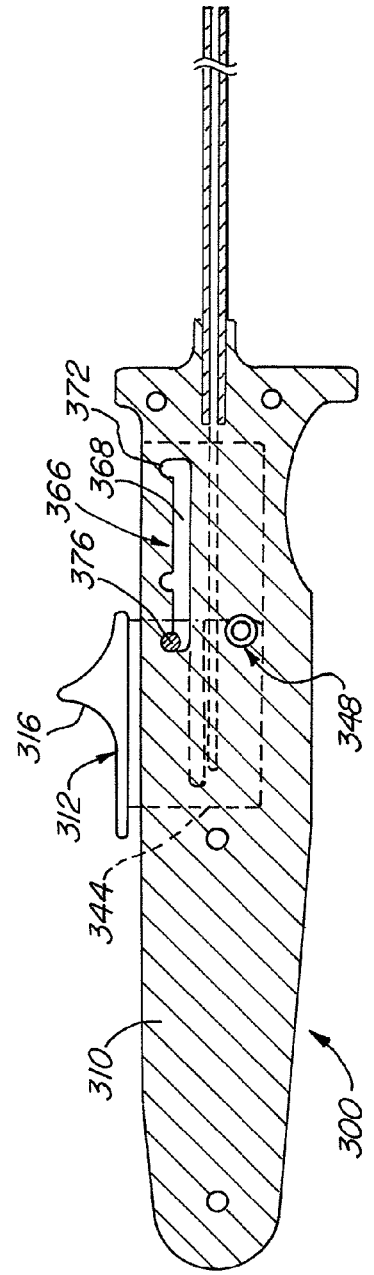

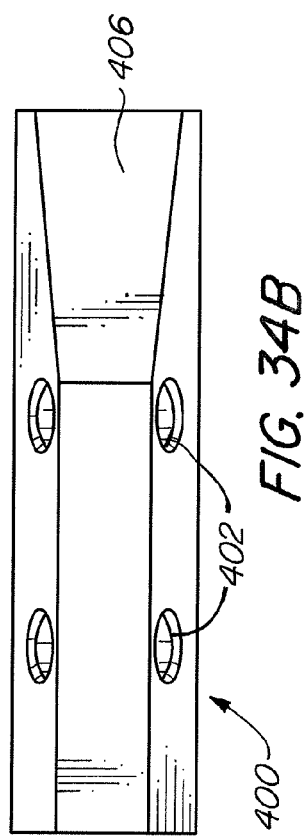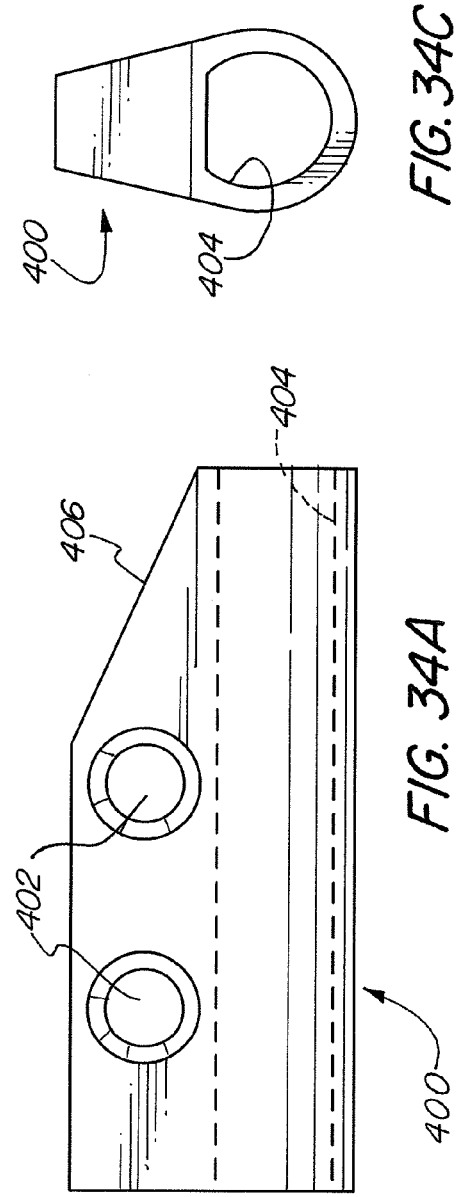

SUTURE HOLDER DELIVERY SYSTEM

FIELD OF THE INVENTION

The present invention relates to suture holders, specifically, suture holders used in soft tissue repair as well as delivery devices and methods for using such holders.

BACKGROUND OF THE INVENTION

When a soft tissue, or a portion of a tissue, such as muscle, ligament, or cartilage, tears, surgery to repair the detached soft tissue is often required. The goal of such surgery is to suture the torn portion of the tissue to thereby repair the tear and reconstitute the tissue back to its original status. Traditionally, repair was accomplished by sewing the tissue together with two needles and a suture, then tying knots to secure the suture within the tissue. To simplify the wound closure procedure and to improve fixation, various types of suture anchors have been developed, such as those described in U.S. Pat. No. 7,153,312 B1 to Torrie et al. and U.S. Pat. No. 6,972,027 B2 to Fallin et al.

Torrie et al. disclose a closure device for repairing a tear in soft tissue comprising a suture coupled with two fixation members. Each fixation member comprises two holes through which the suture is received. The suture is immovably fixed to the first fixation member, but is freely movable relative to the second fixation member. Therefore, a retaining element, in the form of a slip knot or overhand knot, must be provided on the free end of the suture to prevent the suture from loosening between the fixation members when a tension is applied. When an overhand knot is used, the surgeon must use a knot pusher in order to shorten the length of suture between the fixation members and close the tear. As illustrated in FIGS. 2A-2I and 13-13B, the knots required by this system are particularly complicated to tie and correctly position.

Fallin et al. disclose a suture anchor delivery system comprising two suture anchors secured together by a suture. Similar to Torrie et al., the suture is immovably fixed to the first fixation member. The suture is received in the second fixation member such that pulling on the loose end of the suture causes it to selectively lock to the second anchor. Once the fixation members are implanted, tightening the portion of the suture between them requires a highly coordinated procedure. The surgeon must simultaneously pull back on both free ends of a retraction line and the free end of the suture to cause the suture to unlock from the second fixation device. Then, while continuing to pull back on the free end of the suture, the surgeon must slowly release the retraction line at a complementary rate. If necessary, this process is repeated until all of the slack is removed from between the anchors.

Unfortunately, the devices of Torrie et al. and Fallin et al. are unsatisfactory for a variety of reasons. What is desired, therefore, is a suture holding system for use in the repair of soft tissue tears that does not require the use of knots, knot pushers, and retraction lines in order to implant and utilize the devices.

Several devices are also known for the delivery of such suture anchors. Both Fallin et al. and Torrie et al. disclose delivery devices in which two or more suture anchors are delivered via a single needle and single pusher mechanism. Such devices provide the surgeon with little freedom for individually deploying the suture anchors and make it difficult to make adjustments once deployment of the first anchor has begun. As a result, delivery devices which allow for the independent delivery of at least two suture anchors have been developed. For example, U.S. Pat. No. 7,905,904 to Stone et al. discloses a delivery device having separate needles and pushers for delivering each of two implants. However, this device undesirably has the pusher mechanisms extending from opposing surfaces of the body of the device. Further, this device does not provide any means for the surgeon to rigidly fix the position of the delivery needle, which would offer more flexibility in the deployment process. What is desired, therefore, is a suture holding system for use in the repair of soft tissue tears with a delivery device that allows for independent and prioritized deployment of at least two suture anchors that also allows a surgeon to fix one or more of the driver mechanisms in at least one position.

SUMMARY OF THE INVENTION

Accordingly, it is an object of the present invention to provide a suture holder that can selectively lock a suture to the holder without the use of knots or the like.

It is a further object of the present invention to provide a suture holder that can selectively tighten a portion of suture placed across a tear in tissue without the use of retraction lines or the like.

It is yet a further object of the present invention to provide a suture holder that is quickly and easily attached to a suture.

These and other objects and advantages are achieved by providing a suture holding system comprising a block and a suture having a first portion and a second portion. The block has a hole extending therethrough, and a first notch extending along at least a portion of the block. A first suture portion is received in the hole and the first notch and a second suture portion is held against the block by said first suture portion. In some embodiments, the block further comprises a second notch extending along at least a portion of the block and the second suture portion is then at least partially received in the second notch before passing between the first suture portion and the block. The suture holding system may also comprise a second block.

The block is substantially rectangular in shape in some embodiments and may have a tapered edge in others. The block has a length, height, and depth. The block length may be about 2.5 times longer than its height or may be about 3 times longer than its height. The block height may be about 1.5 times longer than its depth or may be about 2 times longer than its depth.

In a further embodiment, the suture holding system comprises a suture having a first portion and a second portion and a block having a first hole extending therethrough, a front surface, a bottom surface, and a top surface. The first suture portion is received in the first hole and passes under the block bottom surface. The second suture portion passes from the bottom surface over the top surface before being held against the block front surface by the first suture portion.

The block may further comprise a notch extending along at least a portion of the top surface of the block, the second suture portion being received in the notch before passing between the first suture portion and the front surface of the block. In another embodiment, the block may further comprise a first notch extending along at least a portion of the bottom surface of the block, the first suture portion being received in the first hole and said the notch. In a further embodiment, the block further comprises a second notch extending along at least a portion of the top surface of the block, the second suture portion being received in the second notch before passing between the first suture portion and the front surface of the block. In yet another embodiment, the block further comprises a second hole extending therethrough, the first suture portion being received in the first hole and the second hole. The block may, in another embodiment, further comprise a notch extending along at least a portion of the top surface of the block, the second suture portion being received in the notch before passing between the first suture portion and the front surface of the block.

A suture holding system comprising a suture having a first portion and a second portion and a first block comprising a first region for receiving a portion of a suture, a second region for receiving a portion of a suture and a third region for receiving a portion of a suture is also provided. The first suture portion is received in the first region and the second region, the second suture portion being at least partially received in the third region before being held against the first block by the first suture portion.

The first region may comprise a hole extending through at least a portion of the first block. The second region may comprise a hole extending through at least a portion of the first block or a notch extending along at least a portion of the first block. The third region may comprise a notch extending along at least a portion of the first block.

A second block for receiving a portion of the suture is also provided. In some embodiments, the second block is rotated 180 degrees with respect to the first block. The second block comprises a fourth region for receiving a portion of a suture, a fifth region for receiving a portion of a suture, and a sixth region for receiving a portion of a suture. The suture further comprises a third portion and a fourth portion, the third suture portion being at least partially received in the fourth region and the fifth region, the fourth suture portion being at least partially received in the sixth region before being held against the second block by the third suture portion.

The fourth region may comprise a hole extending through at least a portion of the second block. The fifth region may comprise a hole extending through at least a portion of the second block or a notch extending along at least a portion of the second block. The sixth region may comprise a notch extending along at least a portion of the second block.

A suture holding system comprising a block having a first hole extending therethrough and a second hole extending therethrough and a suture having a first portion and a second portion is also provided. In this embodiment, the first suture portion is received in the first hole and the second hole, and the second suture portion is held against the block by the first suture portion. In some embodiments, the block may also comprise a notch extending along at least a portion of the block, said second suture portion being received in said notch before passing between said first suture portion and said block.

A suture holder delivery system comprising a housing, a delivery needle at least partially slidably received within the housing, and a driver rod at least partially slidably received within the housing is also provided. In other embodiments, the suture holder delivery system further comprises an actuator in communication with the driver rod. The needle may be curved at the proximal end.

The delivery system further comprises a suture having a first portion and a second portion, and a first block having a hole extending therethrough and a first notch extending along at least a portion of the block. The first suture portion is at least partially received in the hole and the first notch and the second suture portion is held against the block by the first suture portion. In some embodiments, the suture holder delivery system further comprises a second notch extending along at least a portion of the block, the second suture portion being at least partially received in the second notch before passing between the first suture portion and the block.

In some embodiments, the delivery needle has a proximal end and a distal end. In a further embodiment, the driver rod is distal of said first block. In yet another embodiment, the suture holder delivery system comprises a second block, which may be arranged distal of the first block.

In another embodiment, the first block further comprises a longitudinal hole extending therethrough and the needle may be at least partially slidably received within the longitudinal hole. The driver rod may further comprise a tube that is at least partially slidably received over the needle.

In yet another embodiment, the needle comprises an interior passage and the first block and the driver rod may be at least partially slidably received within the needle interior passage.

A method for repairing a tear in soft tissue comprising the steps of placing a first block in a portion of soft tissue, providing a suture having a first portion, a second portion, a proximal end and a connecting portion distal of the first block and passing at least partially through the tear, and pulling on the suture proximal end to shorten the connecting portion of the suture is also provided. The first block has a first region for receiving a portion of a suture, a second region for receiving a portion of a suture, and a third region for receiving a portion of a suture. The first suture portion is at least partially received in the first region and second region, the second suture portion being at least partially received in the third region before passing between the first block and the first suture portion.

The method may further comprise the step of placing a second block into the soft tissue, the suture passing through at least a portion of the second block. The second block may be distal of said first block. The suture connecting portion may be provided between the first block and the second block. The second block may comprise a fourth region for receiving a portion of a suture, a fifth region for receiving a portion of a suture, and a sixth region for receiving a portion of a suture. In a further embodiment, the method further comprises the step of providing a suture having a third portion and a fourth portion, the suture third portion being at least partially received in the fourth region and the fifth region, the suture fourth portion being at least partially received in the sixth region before passing between the second block and the suture third portion.

It is a further object of the present invention to provide an improved device for the delivery of suture anchors such as those described above. A suture anchor delivery system, having a housing with a distal end and a proximal end, a first driver mechanism and a second driver mechanism, each movable in a longitudinal direction with respect to the housing, first and second needles, the first needle connected at a proximal end to the first driver mechanism and the second needle connected at a proximal end to the second driver mechanism, and a toggle assembly operable to fix at least one of the first driver mechanism and second driver mechanism in at least one longitudinal position, may also be provided. The toggle assembly may further include a pin connected at a first end to at least one of the first driver mechanism and second driver mechanism and, an axial channel disposed in the housing, a second end of the pin slidably disposed within the axial channel; and at least one detent open to the channel and adapted to receive the pin. In one embodiment, the toggle assembly has at least three detents spaced longitudinally along the channel. The toggle assembly may be operable to fix a least one of the first driver mechanism and second driver mechanism in at least one of a fully retracted position, a fully extended position and an intermediate position spaced longitudinally between the fully retracted and fully extended positions. In at least some embodiments, both the first driver mechanism and said second driver mechanism may each be fixed by a toggle mechanism in at least one longitudinal position.

The first and second needles of the delivery system may also includes a shoulder for engaging a first suture anchor and a second suture anchor, respectively. The first suture anchor may have a longitudinal bore therein for receiving the first needle therein and the second suture anchor may have a longitudinal bore therein for receiving the second needle therein. A distal portion of each of the first and second needles and the longitudinal bore in the first and second suture anchors may be non-circular in cross-section.

In another embodiment, a suture anchor delivery system including a housing with a distal end and a proximal end, a first driver mechanism and a second driver mechanism, each movable in a longitudinal direction with respect to the housing, a first delivery needle and a second delivery needle, the first delivery needle connected at a proximal end to the first driver mechanism and the second delivery needle connected at a proximal end to the second driver mechanism, the first driver mechanism and the second driver mechanism each having fully retracted and fully extended positions; and a control mechanism operable to prevent the second driver mechanism from being moved in a distal direction until the first driver mechanism is longitudinally advanced to the fully extended position, is also provided. The control mechanism, which may be received in a lateral bore in the housing, is in a locked position until the first driver mechanism is longitudinally advanced to the fully extended position and in an unlocked position after the first driver mechanism is longitudinally advanced to the fully extended position. The control mechanism may include a pin having a head portion and a body portion, and a spring received on the body portion. At least a portion of the pin body portion may be positioned distal of the second driver mechanism when the control mechanism is in a locked position. The spring biases the pin against the first driver portion when the control mechanism is in a locked position. In some embodiments, the delivery device also includes a longitudinal channel positioned within the first driver mechanism. The longitudinal channel may be spaced laterally apart from the second driver mechanism and the head of the pin is moved laterally and is received within the channel when the control mechanism is in an unlocked position. Each of the first driver mechanism and second driver mechanism may also include a slider coupled to and extending from a top surface of the body.

In yet another embodiment, a suture anchor delivery system, including a housing having a distal end and a proximal end, a first driver mechanism and a second driver mechanism, each movable in a longitudinal direction with respect to the housing, a first delivery needle and a second delivery needle, the first delivery needle connected at a proximal end to the first driver mechanism and the second delivery needle connected at a proximal end to the second driver mechanism, the first driver mechanism and said second driver mechanism each having fully retracted and fully extended positions; a toggle assembly operable to fix at least one of the first driver mechanism and second driver mechanism in at least one longitudinal position; and a locking mechanism operable to prevent the second driver mechanism from being moved in a distal direction until the first driver mechanism is longitudinally advanced to the fully extended position may also be provided.

BRIEF DESCRIPTION OF THE DRAWINGS

FIG. 13 is a side view of an embodiment of the delivery device for use with the suture holding system of the present invention.

FIG. 14 is a partial top view of an embodiment of the delivery device for use with the suture holding system of the present invention.

FIG. 15 is a partial side sectional view, taken along line A, of an embodiment of the delivery device for use with the suture holding system of the present invention.

FIG. 21A is a side view of an embodiment of the suture holding system of the present invention.

FIG. 21B is a is a front view of an embodiment of the suture holding system of the present invention.

FIG. 22 is a projected view of an embodiment of the delivery device of the present invention.

FIG. 23A is a side view of an embodiment of the delivery device shown in FIG. 22.

FIG. 23B is a top view of an embodiment of the delivery device shown in FIG. 22.

FIG. 24A is a sectional view of an embodiment of the delivery device shown in FIG. 23A taken along the line A-A.

FIG. 24B is a sectional view of an embodiment of the delivery device shown in FIG. 23B taken along the line B-B.

FIG. 27A is a side view of an embodiment of the delivery device shown in FIG. 22.

FIG. 27B is a top view of an embodiment of the delivery device shown in FIG. 22.

FIG. 28A is a sectional view of an embodiment of the delivery device shown in FIG. 27A taken along the line D-D.

FIG. 28B is a sectional view of an embodiment of the delivery device shown in FIG. 27B taken along the line E-E.

FIG. 30A is a side view of an embodiment of the delivery device shown in FIG. 22.

FIG. 30B is a top view of an embodiment of the delivery device shown in FIG. 22.

FIG. 31A is a sectional view of an embodiment of the delivery device shown in FIG. 30A taken along the line G-G.

FIG. 31B is a sectional view of an embodiment of the delivery device shown in FIG. 30B taken along the line I-I.

FIG. 34A is a side view of an embodiment of a suture anchor of the present invention for use with the delivery device depicted in FIG. 22.

FIG. 34B is a top view of an embodiment of a suture anchor of the present invention for use with the delivery device depicted in FIG. 22.

FIG. 34C is a back view of an embodiment of a suture anchor of the present invention for use with the delivery device depicted in FIG. 22.

DETAILED DESCRIPTION OF THE INVENTION

Figure 1:
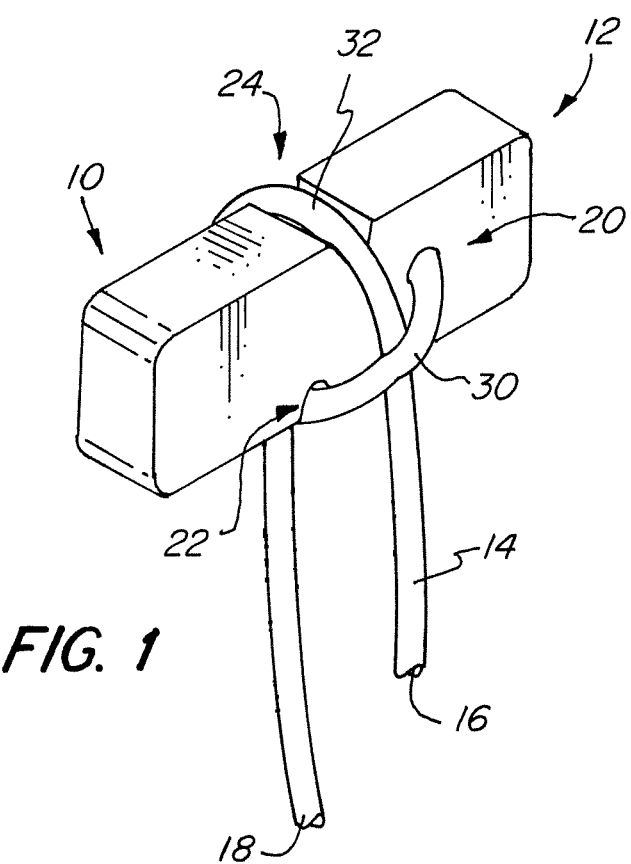
FIG. 1 is a perspective view of an embodiment of the suture holding system of the present invention.
Figure 2:
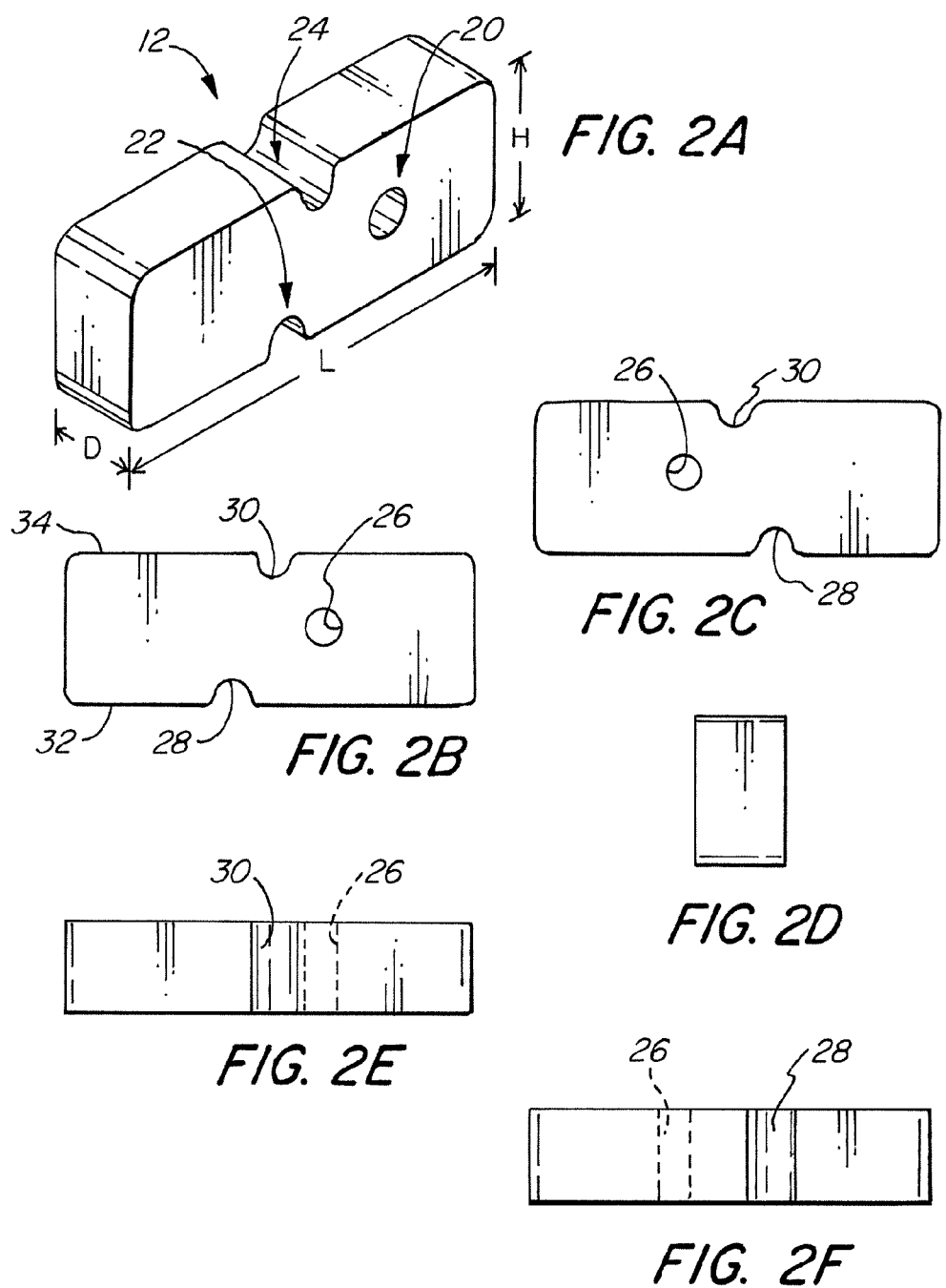
FIG. 2A is a perspective view of an embodiment of the block as used in the suture holding system of the present invention.
FIG. 2B is a front view of an embodiment of the block as used in the suture holding system of the present invention.
FIG. 2C is a back view of an embodiment of the block as used in the suture holding system of the present invention.
FIG. 2D is a side view of an embodiment of the block as used in the suture holding system of the present invention.
FIG. 2E is a top view of an embodiment of the block as used in the suture holding system of the present invention.
FIG. 2F is a bottom view of an embodiment of the block as used in the suture holding system of the present invention.

The novel suture holding system 10 of the present invention, comprising a block 12 and a suture 14 having proximal 16 and distal 18 ends, is depicted in FIG. 1. Block 12 defines first 20, second 22, and third 24 regions for receiving a portion of suture 14. In one embodiment, first region 20 is provided as a hole 26 extending through the block 12, second region 22 is provided as a notch 28 on the bottom surface 32 of the block 12, and third region 24 is provided as a notch 30 on the top surface 34 of the block 12. As used in the specification and appended claims, the term "suture" is intended to include any type of flexible line, but typically comprises medical grade suture.

As shown in FIGS. 2A-2F, block 12 is generally rectangular in cross section and profile, having a length L, height H and depth D. In alternative embodiments, it is appreciated that the edges of block 12 may be rounded or chamfered. The block length can range from about 2.5 to about 3 times longer than the block height. The block height can range from about 1.5 to about 2 times longer than the block depth. In a preferred embodiment, the block is 7 mm long, 2.4 mm high, and 1.5 mm deep. In another preferred embodiment, shown in FIGS. 18A-18F, the block is 5 mm long, 2 mm high, and 1.2 mm deep. Other block shapes and dimensions are possible and are contemplated herein as alternative embodiments.

Figure 3:
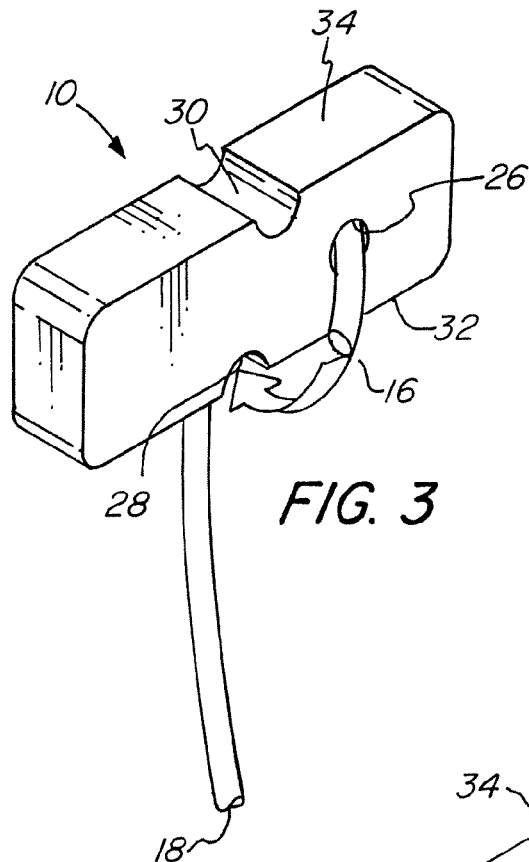
FIG. 3 is a perspective view of an embodiment of the suture holding system of the present invention, demonstrating how the suture is attached to the block.
Figure 4:
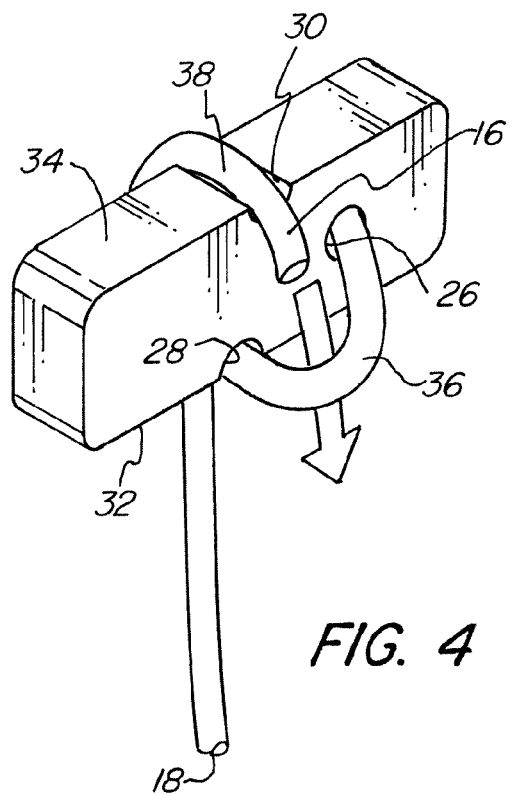
FIG. 4 is a perspective view of an embodiment of the suture holding system of the present invention, demonstrating how the suture is attached to the block.

Referring now to FIGS. 3 and 4, suture 14 is attached to block 12 by threading proximal end 16 of suture 14 through hole 26 and then through notch 28, defining a first suture portion 36. Proximal end 16 is then wrapped around the block 12 and received in notch 30 before passing between first suture portion 36 and the block 12, defining a second suture portion 38. In this configuration, pulling on distal end 18 of suture 14 selectively locks suture 14 to block 12 without the need for any type of knot or retaining element. When distal end 18 of suture 14 is pulled taught, first suture portion 36 tightens, pressing second suture portion 38 against the block 12 and preventing the suture 14 from advancing further in the distal direction. However, pulling proximal end 16 of suture 14 allows the suture 14 to advance freely in the proximal direction.

Figure 5:
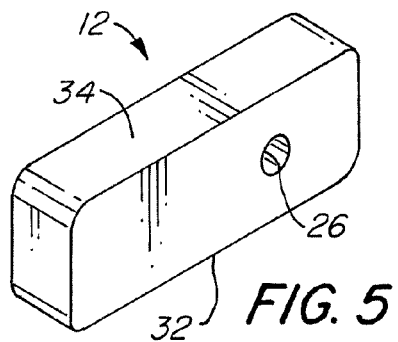
FIG. 5 is a perspective view of an embodiment of the block as used in the suture holding system of the present invention.
Figure 10:
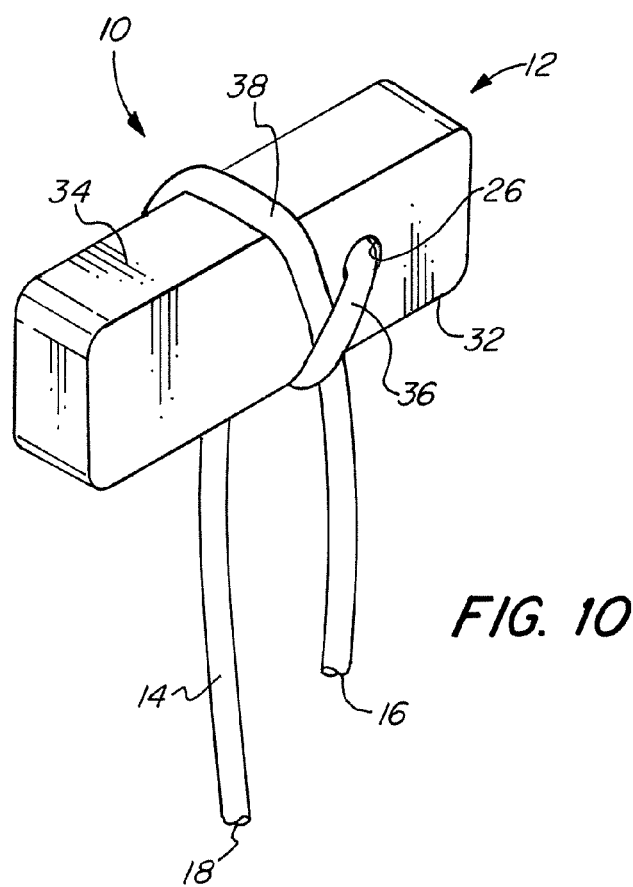
FIG. 10 is a perspective view of an embodiment of the suture holding system of the present invention.

Many other operative configurations of the first 20, second 22, and third 24 regions of block 12, in addition to the combination shown in FIG. 1, are contemplated herein. For example, in the embodiment of FIG. 5, first region 20 is provided as a hole 26, second region 22 is the bottom surface 32 of the block 14, and third region 24 is the top surface 34 of the block 14. In this configuration, as shown in FIG. 10, suture 14 is attached to block 12 by threading the proximal end 16 of suture 14 through hole 26 and then under the bottom surface 32 of block 12, defining first suture portion 36. Proximal end 16 is then wrapped around the block 12 and over the top surface 34 before passing between first suture portion 36 and the block 12, defining a second suture portion 38. Again, when distal end 18 of suture 14 is pulled taught first suture portion 36 tightens, pressing second suture portion 38 against the block 12 and preventing the suture 14 from advancing in the distal direction.

Figure 6:
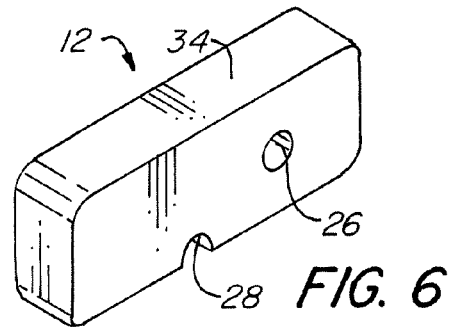
FIG. 6 is a perspective view of an embodiment of the block as used in the suture holding system of the present invention.
Figure 7:
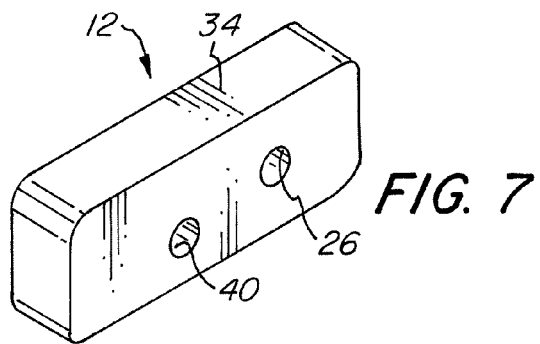
FIG. 7 is a perspective view of an embodiment of the block as used in the suture holding system of the present invention.
Figure 8:
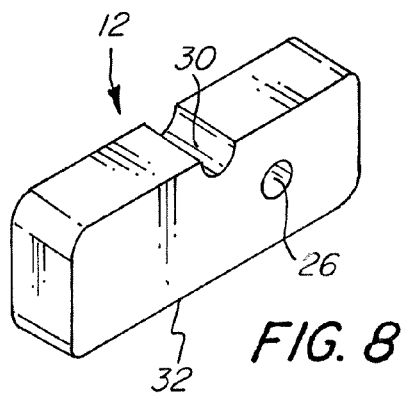
FIG. 8 is a perspective view of an embodiment of the block as used in the suture holding system of the present invention.
Figure 9:
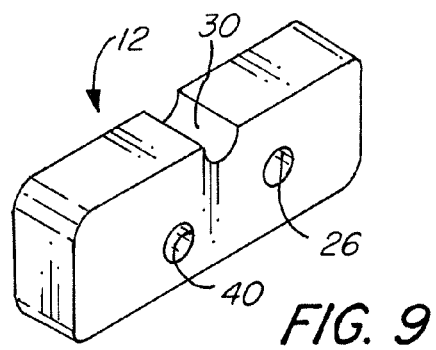
FIG. 9 is a perspective view of an embodiment of the block as used in the suture holding system of the present invention.

Other configurations include hole 26, notch 28 and the top surface 34 of the block 12 (FIG. 6); hole 26, hole 40, and the top surface 34 of the block 12 (FIG. 7); hole 26, the bottom surface 32 of the block 12, and notch 30 (FIG. 8); and hole 26, hole 40, and notch 30 (FIG. 9). The particular position of the holes and notches on the block 12 shown in these figures is merely exemplary and other positions are possible without loss of functionality of the block 12. It is also appreciated that first 20, second 22, and third 24 regions may be inverted without any loss in functionality such that third region 24 is oriented near bottom surface 32.

Figure 11:
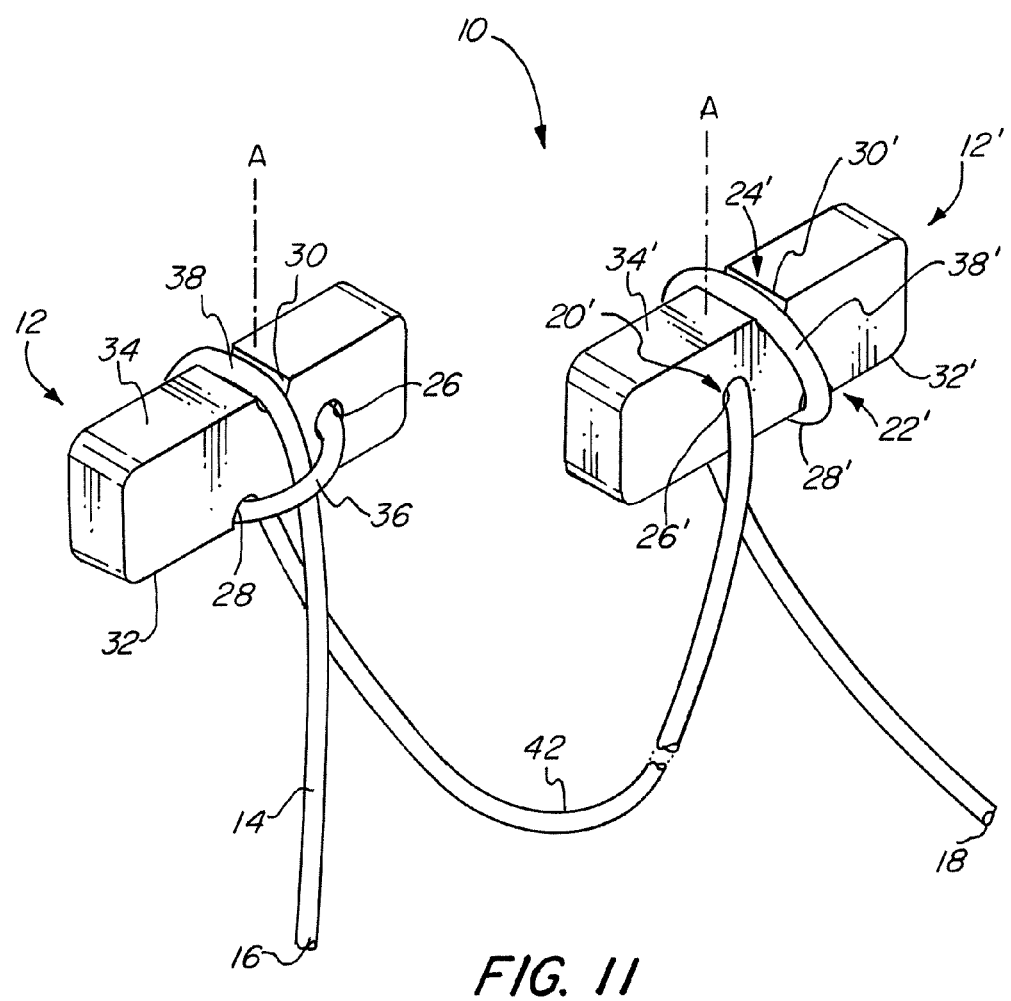
FIG. 11 is a perspective view of an embodiment of the suture holding system of the present invention having two blocks.

The suture holding system 10 of the present invention may also comprise a second block 12'. Referring now to FIG. 11, second block 12' is rotated 180 degrees with respect to first block 12 around an axis A and defines first 20', second 22', and third 24' regions for receiving a portion of suture 14. In one embodiment, first region 20' is provided as a hole 26' extending through block 12', second region 22' is provided as a notch 28' on the bottom surface 32' of block 12', and third region 24' is provided as a notch 30' on the top surface 34' of block 12'. Second block 12' may have any of the above-described alternative configurations as block 12.

Figure 12:
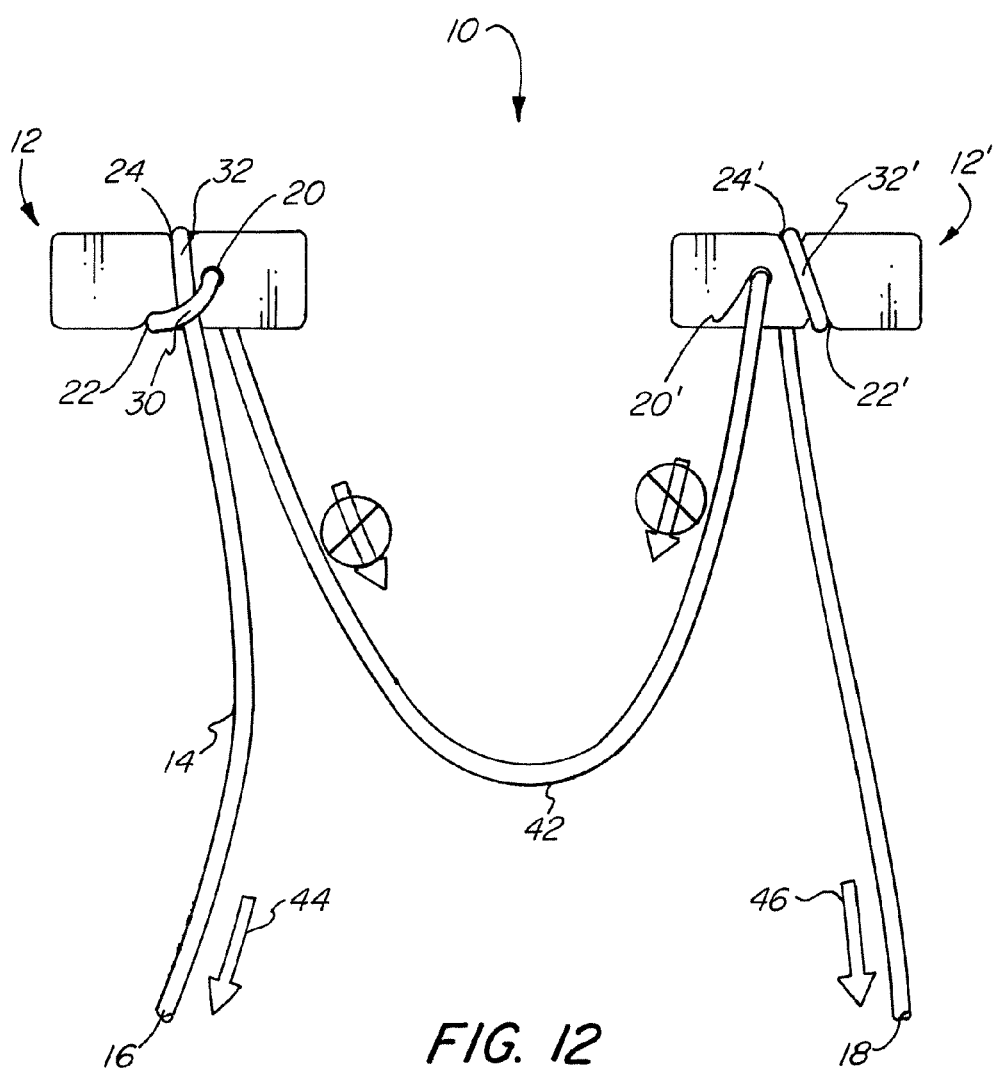
FIG. 12 is a front view of an embodiment of the suture holding system of the present invention, illustrating the selective locking of the suture with respect to each block.

Suture 14 is attached to block 12 as described above. As shown in FIG. 11, suture 14 is then attached to block 12' by threading distal end 18 through hole 26' and then through notch 28', defining a first suture portion 36' (not shown). Distal end 18 is then wrapped around the block 12' and received in notch 30' before passing between first suture portion 36' and the block 12', defining a second suture portion 38'. A connecting portion 42 of the suture 14 is defined between block 12 and block 12'. The configuration of first 22, 22', second 24, 24' and third 26, 26' regions, and the rotation of second block 12' with respect to first block 12", allows suture 14 to be pulled in the direction of arrows 44 and 46, but does not allow tension placed on connecting portion 42 to pull suture 14 in the opposite direction through the blocks 12, 12'. This is illustrated in FIG. 12.

A delivery device 50 configured for implanting the blocks 12, 12' of the suture holding system 10 into soft tissue so as to facilitate repair of a tear in soft tissue is shown in FIGS. 13-15. Delivery device 50 comprises a needle 54 and a driver rod 56, both at least partially slidably received within a housing 58, and a handle 52. Handle 52 may have a variety of cross sectional shapes, such as, but not limited to, circular, square, rectangular, oblong, triangular, and the like. Needle 54 has a hollow interior passage 60 and both the driver rod 56 and suture holding system 10 are slidably received therein. Proximal end 62 of the needle 54 may be closed, and preferably, may terminate in a pointed tip 64 to aid in penetration of the tissue. In the embodiment shown in FIG. 15, needle 54 is curved upward at its proximal end 62. It will be appreciated that depending on the intended use of the suture holding system 10, the proximal end 62 of needle 54 may be straight along its length, or may be curved or bent into a variety of alternative configurations.

Needle 54 is typically made of a metal, such a stainless steel, but can also be made of plastic, composite, or other desired material. Where needle 54 is straight, driver rod 56 can be made of the same material as needle 54. Where needle 54 is curved, however, driver rod 56 is typically made of a material stiff enough to advance a block 12 of suture holding system 10 through interior passage 60, but flexible enough to conform to the contour of needle 54. For example, driver rod 56 may be composed of spring stainless steel or nitinol.

In this embodiment, a slot 66 is formed in needle 54 in communication with interior passage 60 to allow suture holding system 10 to exit the needle. Slot 66 terminates in a sloped wall 68 distal of needle tip 64. This sloped wall 66 helps to flip the suture holder system 10 when it is implanted in the tissue, the benefit of which will be described further below. In alternative embodiments, it is appreciated that slot 66 extend distally to the end of the needle 54, or can terminate at any point before, so long as slot 66 is large enough to accommodate suture holding system 10. Driver rod 56 is disposed distal of block 12 within the interior passage 60 and acts to advance block 12 through the passage 60 and out through slot 66.

Housing 58 is slidably received in proximal end 74 of handle 52. In one embodiment, housing 58 is provided as a depth limiter with calibration bands 70, which determine the penetration depth of needle 54 into the tissue. Locking nut 72 is tightened once the desired depth is chosen. Handle 52 includes an actuating slider 76 attached to driver rod 56 for advancing driver rod 56 towards the proximal end 62 of the needle 54. Last, reload knob 78 is provided at the distal end 80 of handle 52 and is attached to the distal end of the needle 54. Pulling back on reload knob 78 causes needle 54 to retract distally into housing 58, the function of which will be described below.

Figure 16:
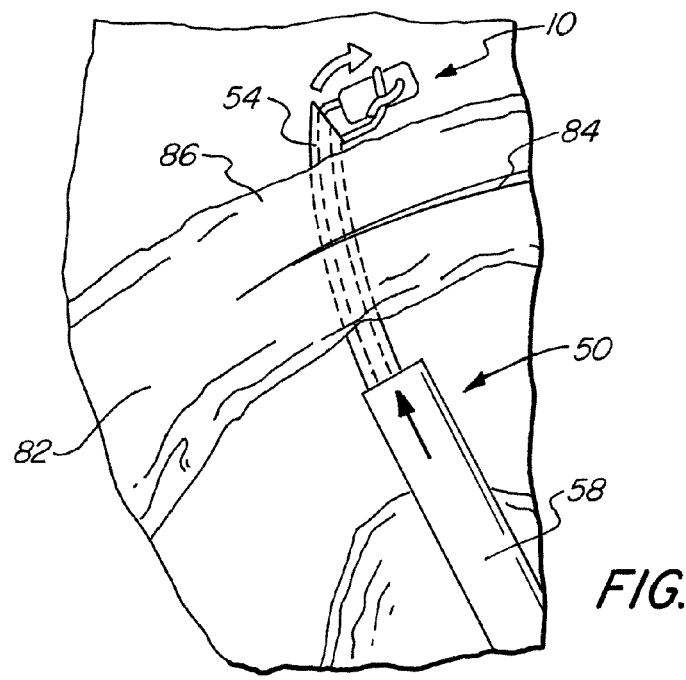
FIG. 16 is a view of an embodiment of the suture holding system and an embodiment of the delivery device of the present invention, being used to repair a tear in soft tissue.
Figure 17:
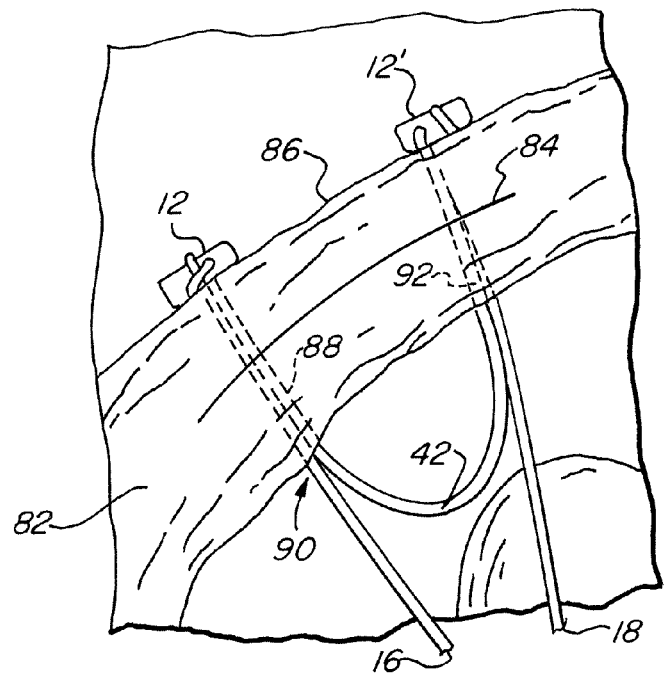
FIG. 17 is a view of an embodiment of the suture holding system having two blocks and an embodiment of the delivery device of the present invention, being used to repair a tear in soft tissue.

In use, suture 14 is attached to first block 12 and second block 12' and first block 12 is loaded into the interior passage 60 of needle 54 through slot 66. Second block 12' inserted into housing 58, such as into a recess or slot (not shown). Referring now to FIGS. 16 and 17, after suture holding system 10 is loaded into delivery device 50, a user inserts delivery device 50 into, for example, the knee joint, and passes needle 54 through soft tissue 82 and across tear 84 until needle tip 64 and first block 12 extend through tissue surface 86. The user then advances slider 76 to actuate driver rod 56 and advance first block 12 out through slot 66 of needle 54, causing first block 12 to flip. By flipping the block 12, it is ensured that the elongated bottom surface 32 of the block 12 is biased against the top surface 86 of the tissue so that the block 12 does not unintentionally pass through the puncture formed by the needle 54. Delivery device 50 and needle 54 are removed from tissue 82, leaving first block 12 remaining on the surface 86. During retraction of needle 54, a portion of suture 14 is played out of delivery device 50, with connecting portion 42 making a first pass 88 through soft tissue 82 across tear 84.

To load second block 12' into needle 54, the user pulls back on reload knob 78 to retract needle 54 and driver rod 56 into housing 58. Second block 12' is loaded into interior passage 60 through slot 66, and the user returns reload knob 78 to its original position. Needle 54 is then inserted through tissue 82, at a point spaced apart from exit point 90, across tear 84 until needle tip 64 and second block 12' extend through tissue surface 86. The user then advances slider 76 to actuate driver rod 56 and advance second block 12' out through slot 66 of needle 54, causing second block 12' to flip so that its bottom surface 32' comes to rest on tissue surface 86. Delivery device 50 and needle 54 are removed from tissue 82, leaving second block 12' remaining on the surface 86, as described above with reference to first block 12. Connecting portion 42 of suture 14 now makes a second pass 92 through soft tissue 82 across tear 84.

Proximal 16 and distal 18 ends of suture 14 now extend from tissue 82. The user grasps ends 16, 18 by hand or with forceps and pulls to shorten connecting portion 42 of suture 14 to the desired length and close tear 84. Excess suture 14 can then be trimmed off. Because suture 14 will lock against the blocks 12, 12' when any tension is placed on the connecting portion 42 of the suture 14, the free ends of the suture do not need to be knotted or tied off. This also obviates the need for a knot pusher to tighten the suture across the tear.

With the suture holding system 10 of the present invention, it is also possible to close a tear in the tissue through the use of only one block, in which case a retaining element, such as a knot, or other device would be placed on distal end 18 of suture 14 to allow the suture 14 to be tightened across the tear 84 and prevent it from loosening.

Figure 18A:
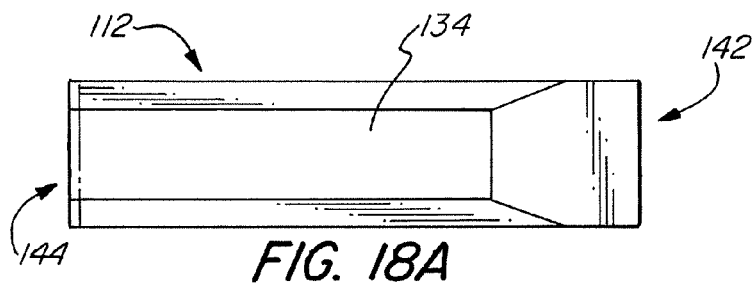
FIG. 18A is a top view of an embodiment of the block as used in the suture holding system of the present invention.
Figure 18B:
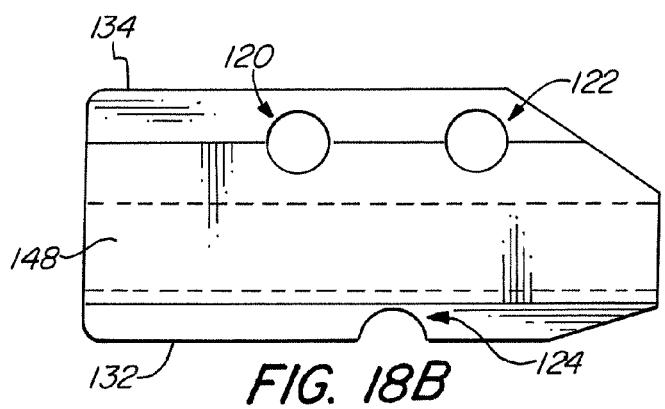
FIG. 18B is a side view of an embodiment of the block as used in the suture holding system of the present invention.
Figure 18E:
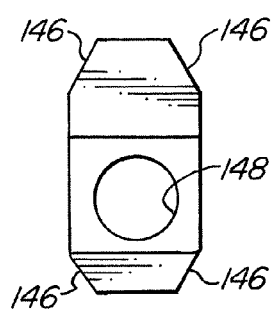
FIG. 18E is a side view of an embodiment of the block as used in the suture holding system of the present invention.
Figure 18C:
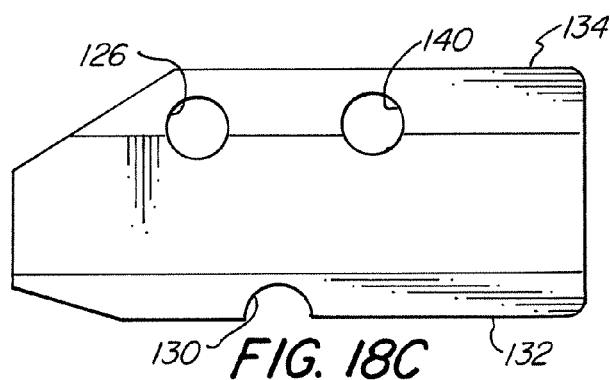
FIG. 18C is a side view of an embodiment of the block as used in the suture holding system of the present invention.
Figure 18F:
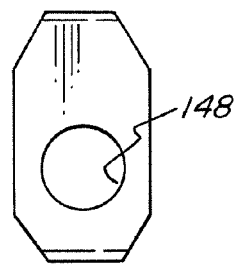
FIG. 18F is a side view of an embodiment of the block as used in the suture holding system of the present invention.
Figure 18D:
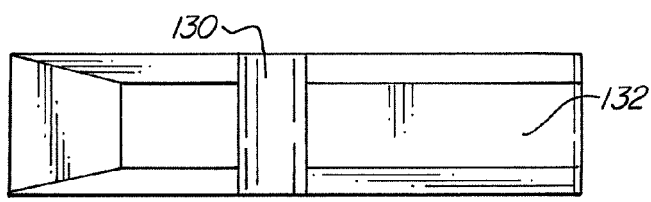
FIG. 18D is a bottom view of an embodiment of the block as used in the suture holding system of the present invention.

FIGS. 18A-18F depict an additional embodiment of the suture holding system 110 of the present invention. As shown, block 112, having bottom surface 132 and top surface 134, defines first 120, second 122 and third 124 regions for receiving a portion of suture 14. In this embodiment, first region 120 is provided as a hole 126, second region 122 is provided as a hole 140, and third region 124 is provided as a notch 130 along the bottom surface 132 of the block 112. To aid in implantation of the block 112, as will be described further below, the proximal end 142 of the block 112 is tapered back towards the distal end 144 on both the top 134 and bottom 132 surfaces. Similarly, as shown in FIGS. 18E and 18F, the four corner edges 146 are beveled to give the block 114 a more rounded cross section. Block 112 is also provided with a longitudinal hole 148 for receiving a delivery needle 154.

Figure 19:
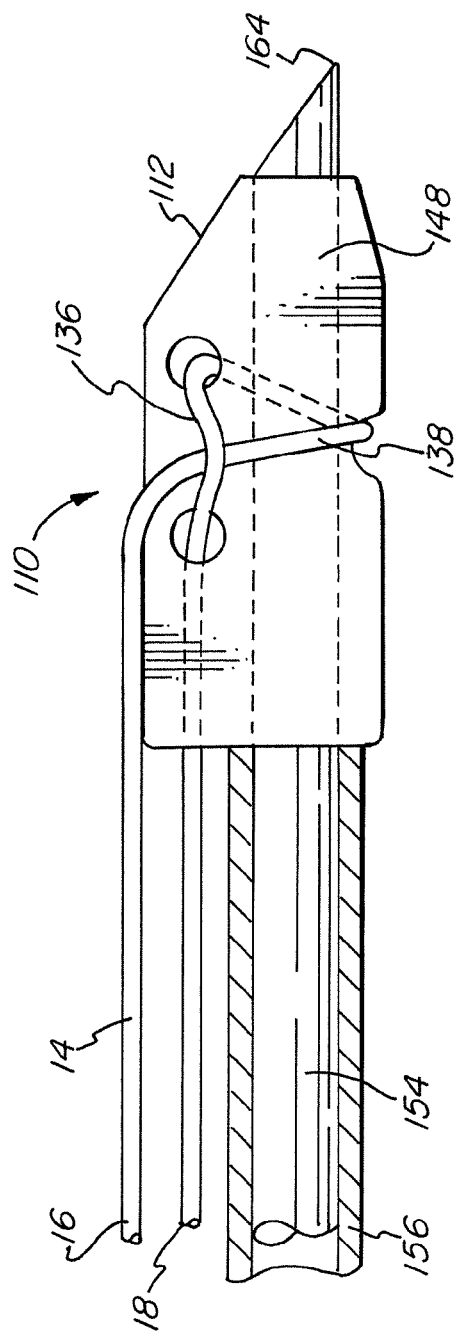
FIG. 19 is a side view of an embodiment of the suture holding system and a partial side view of an embodiment of the delivery device of the present invention.

As shown in FIG. 19, suture 14 is attached to block 112 by threading the proximal end 16 of suture 14 through hole 126 and then through hole 140, defining first suture portion 136. Proximal end 16 is then wrapped down and received in notch 130 before passing between first suture portion 136 and the block 112, defining a second suture portion 138. Again, when distal end 18 of suture 14 is pulled taught first suture portion 136 tightens, pressing second suture portion 138 against the block 112 and preventing the suture 14 from advancing in the distal direction. Block 112 may take on any of the additional block configurations described above and shown in FIGS. 5-9.

In this embodiment, needle 154, having pointed tip 164, is slidably received in hole 148 of block 112. Driver rod 156, being hollow in this embodiment, is slid over needle 154 until it abuts distal end 144 of block 112. As described above, needle 154 may also be curved at its proximal end. Driver rod 156 and needle 154 are slidably received in housing 158 of the delivery device 150. A second block 112', if desired, connected to first block 112 by suture 14, is received in recess 159 within housing 158 until it is ready to be implanted. In use, delivery system 150 operates and functions in the same manner described above and as depicted in FIGS. 16 and 17 to implant blocks 112 and 112'.

FIGS. 21A and 21B depict another embodiment of the suture holding system 210 of the present invention. As shown, block 212 having bottom surface 232 and top surface 234, defines first 220, second 222, third 224, and fourth 225 regions for receiving a portion of suture 14. In this embodiment, first region 220 is provided as a hole 226, second region 222 is provided as a hole 240, third region 224 is provided as a notch 230 along the top surface 234 of the block 212, and fourth region 225 is provided as a hole 231. To aid in implantation of the block 212 the proximal end 242 is tapered back towards the distal end 244 on the top surface 234. Similarly, as shown in FIG. 21B, the top corner edges 246 are beveled.

Block 212 is also provided with a square-shaped longitudinal hole 248 for receiving a delivery needle. In this embodiment, the delivery needle would also be square. By providing the delivery needle and the longitudinal hole 248 with a square shape, the block 212 will be prevented from rotating about the delivery needle during insertion of the suture holding system 210 into the tissue. It is appreciated that any non-circular longitudinal hole and delivery needle could be used to accomplish this goal.

As shown in FIG. 21A, suture 14 is attached to block 212 by threading the proximal end 16 of suture 14 through hole 226 and then through hole 240, defining first suture portion 236. Proximal end 16 is then wrapped around the back of the block 212 and received in notch 230 before passing between first suture portion 236 and the block 212, defining a second suture portion 238. Proximal end 16 is then passed through hole 231. Again, when distal end 18 of suture 14 is pulled taught first suture portion 236 tightens, pressing second suture portion 238 against the block 212 and preventing the suture 14 from advancing in the distal direction. Block 212 may take on any of the additional block configurations described above and shown in FIGS. 5-9.

Figure 20:
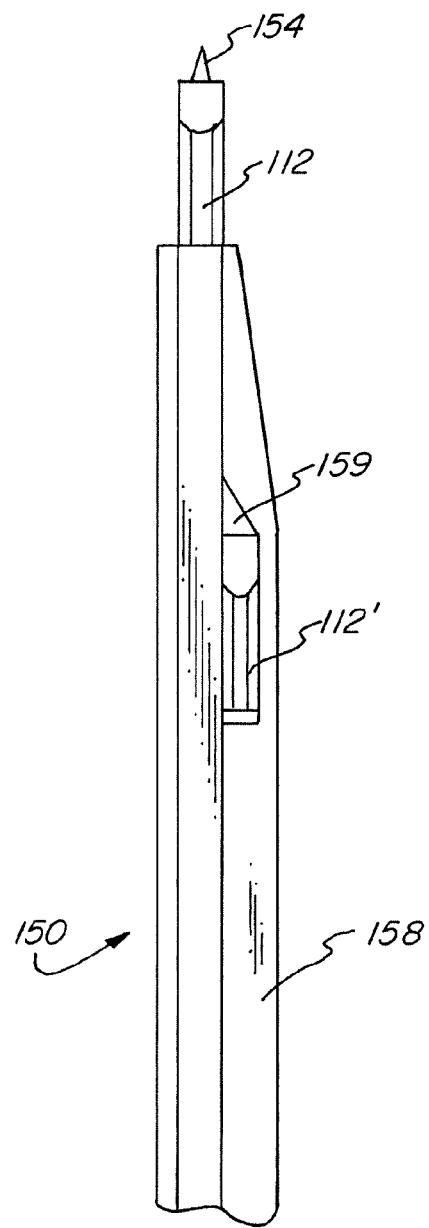
FIG. 20 is a side view of an embodiment of the suture holding system and a partial side view of an embodiment of the delivery device of the present invention.
Figure 25:
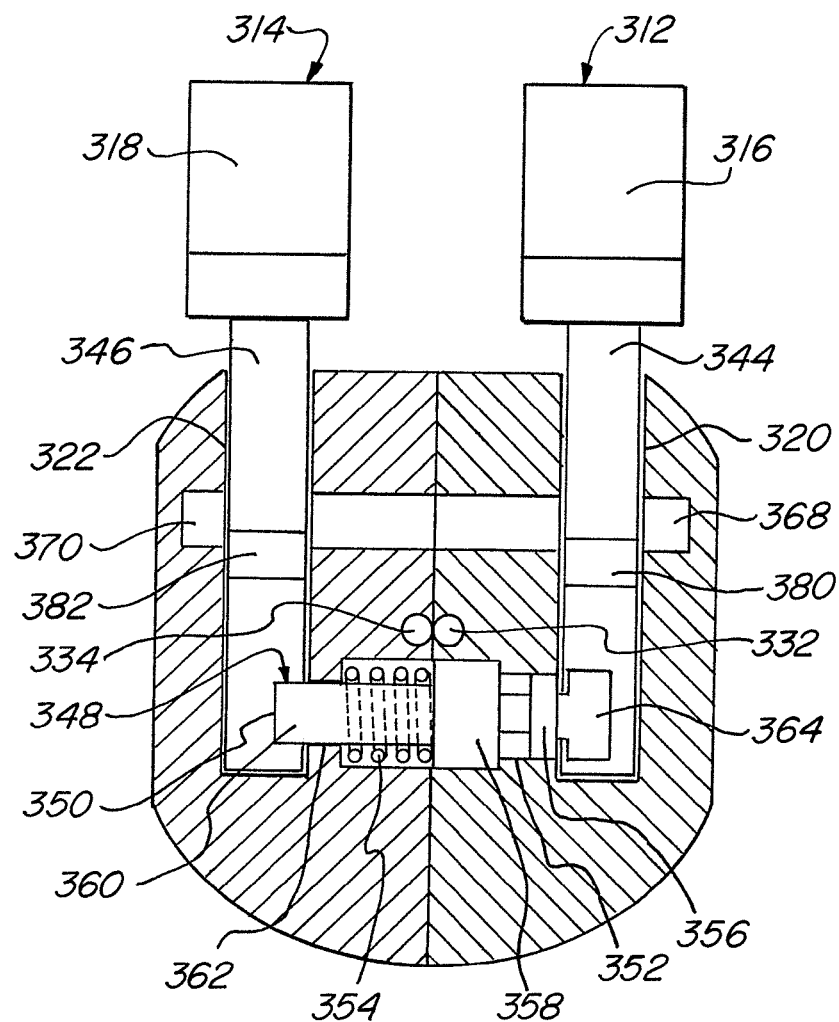
FIG. 25 is a sectional view of an embodiment of the delivery device shown in FIG. 23B taken along the line C-C.

Block 212 is implanted into tissue in the same manner as described above with respect to the embodiment shown in FIGS. 18-20 and may also be used with a second block.

Figure 26:
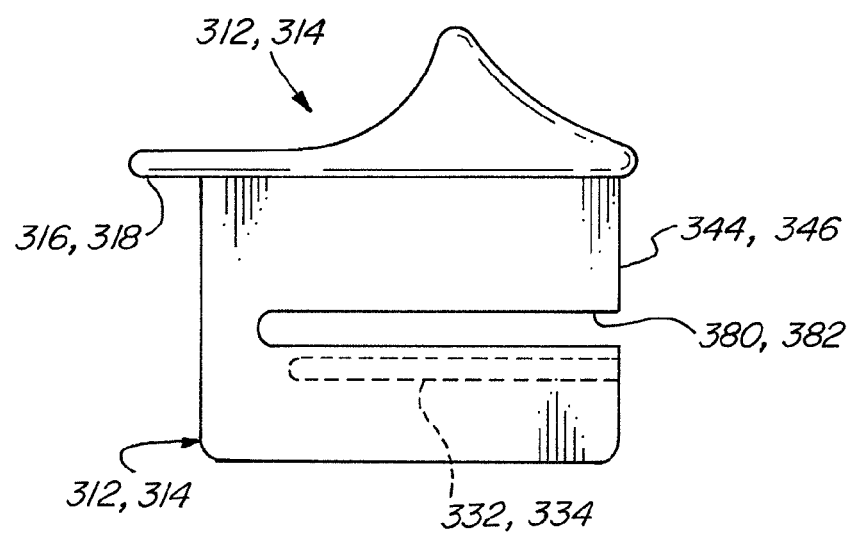
FIG. 26 is a side view of an embodiment of the driver mechanism for use in the delivery device of FIG. 22.

An additional embodiment of a delivery device 300 is shown in FIG. 22. The delivery device 300 includes a housing 310, which may be formed in two separate pieces and connected together or may be formed as one continuous piece, with first 312 and second 314 driver mechanisms coupled thereto for independently deploying two suture anchors (not shown). The driver mechanisms 312, 314 are slidably disposed in first 320 and second 322 channels open to the top surface 324 of the housing 310 and include first 316 and second 318 pushers. Grips 326 may be provided on the pushers 316, 318 to prevent the surgeon's fingers or thumb from slipping during deployment. A finger hold 328 may also be provided on the bottom surface 330 of the housing 310. As shown in detail in FIG. 26, first 312 and second 314 driver mechanisms also include first 344 and second 346 fins, respectively, extending downwardly from the pushers 316, 318. The fins 344, 346 are slidably received within channels 320, 322.

First 332 and second 334 delivery needles for carrying the two suture anchors are coupled to the driver mechanisms 312 and 314 by conventional means and extend through a cannula 336 which may be provided at a distal end 338 of the housing 310. The distal end 342 of the cannula 336 may be forked to allow for passage of a suture connecting the two anchors. Additionally, the distal end of the cannula 342 and the distal end of the needles 332, 334 may have a slight curvature to aid in implanting to the suture anchors. Calibration marks 340, which determine the penetration depth of needle, may be provided on the top surface 324 of the housing for assisting the surgeon.

The improved delivery device 300 also includes a control mechanism 344 for controlling the sequence of deployment of the driver mechanisms 312, 314. Specifically, the control 344 ensures that the first driver mechanism 312 is deployed before the second driver mechanism 312, such that the first suture anchor is implanted before the second suture anchor. This sequence of implantation is important for maintaining the orientation of the first suture anchor with respect to the second suture anchor so that the suture threaded between the two anchors does not become tangled, twisted or reversed, which will make tightening of the suture and repair of the torn tissue difficult, if not impossible.

Generally, the control mechanism 344 does not allow the second driver mechanism 314 to be advanced in a lateral direction until the first driver mechanism 312 has been advanced to a fully extended position and the first suture anchor is implanted. FIGS. 23A, 23B, 24A, 24B and 25 illustrate both driver mechanisms 312, 314 in a fully retracted position. In this position, needles 332, 334 are concealed within the cannula 336.

In one embodiment, the control mechanism 348 includes a pin 350 slidably disposed in a lateral bore 352 in the housing 310. As shown in FIG. 24A, when the first driver mechanism 312 is fully retracted, spring 354, keeps the head 356 of pin 350 biased towards the fin 344 of the first driver mechanism. In this position, one end of the pin 350 lies distal of the fin 346 of the second driver mechanism 314, preventing it from moving in a distal direction. The pin 350 also includes a stop 358, having a diameter conforming approximately to the diameter of the bore 352 and is larger than the diameter of the body portion 360 of the pin.

Figure 29:
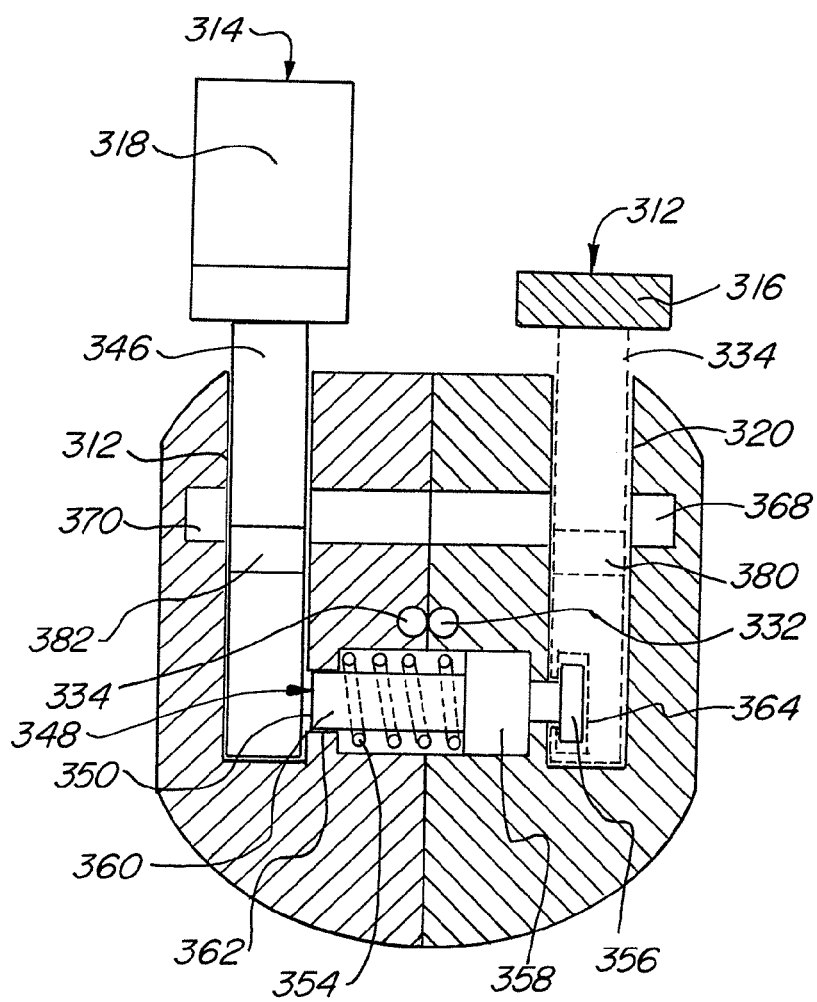
FIG. 29 is a sectional view of an embodiment of the delivery device shown in FIG. 27B taken along the line F-F.
Figure 32:
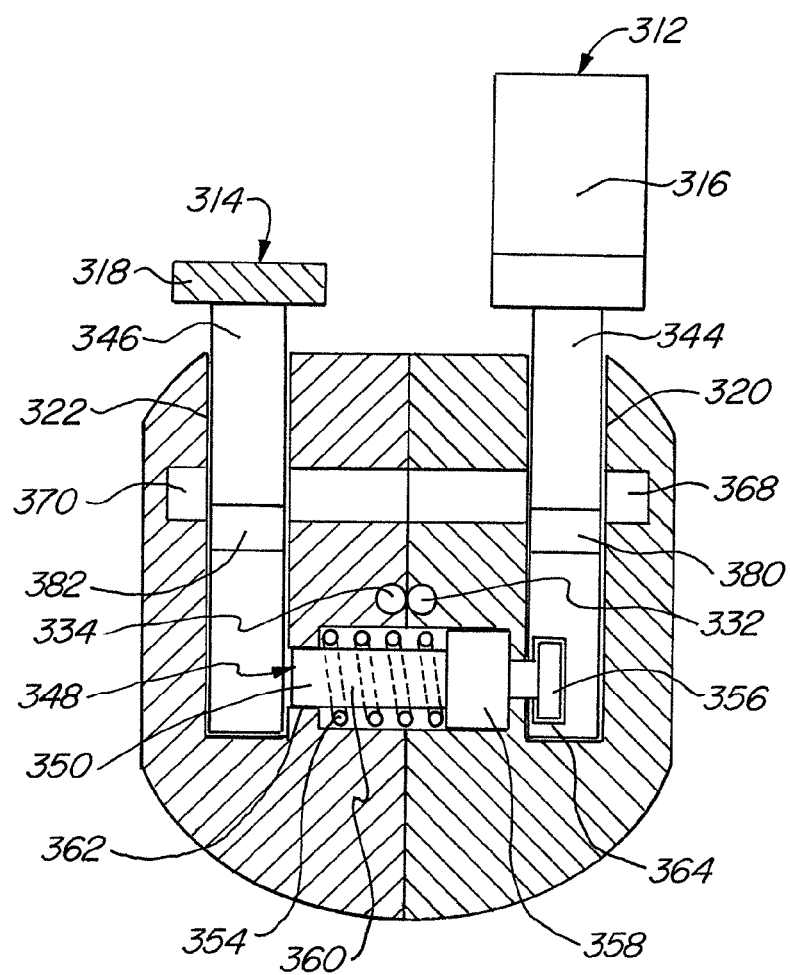
FIG. 32 is a sectional view of an embodiment of the delivery device shown in FIG. 30B taken along the line I-I.

FIGS. 27A, 27B, 28A, 28B and 29 illustrate the first driver mechanism 312 in a fully extended position, while the second driver mechanism 314 remains in a fully retracted position. Until the first driver mechanism 312 is moved into this position, the second driver mechanism 314 cannot be advanced. As shown in FIG. 28A, when the first driver mechanism 312 is fully advanced, the fin 344 is moved completely distal of the pin head 356, allowing clearance from the lateral bore 352, into the channel 320. Spring 354, having been compressed in the locked position of the control mechanism 334, now causes the pin to move laterally into the channel 320. As shown in FIG. 29, a track 364, which runs the length of fin 344, is also provided. When the surgeon chooses to return the first driver mechanism 312 from the fully extended to the fully retracted position, the head 356 will pass through track 364. Once pin 350 has moves laterally into channel 320, the second end of the pin no longer blocks second driver mechanism 314 from moving longitudinally in channel 312 and the surgeon may implant the second suture anchor.

In FIGS. 30A, 30B, 31A, 31B and 32, first driver mechanism 312 has been returned to a fully retracted state and the second driver mechanism 314 is advanced to a fully extended state, thus allowing the surgeon to implant the second suture anchor.

The delivery device 300 may also be provided with a toggle mechanism 366. It is often desirable for the surgeon to fix or lock a driver mechanism, and thus a delivery needle, in a particular position during the implantation procedure. For example, the surgeon may wish to fix the driver mechanism in a fully extended position, or in an intermediate position in between the fully retracted and fully extended positions. This ability to fix the driver mechanism provides additional rigidity to the delivery device in that the surgeon need not physically hold the pusher in the desired position. Further, the ability to fix the driver mechanism in an intermediate position, where the delivery needle is not fully extended, provides the surgeon with the flexibility to change the position of the needle within the tissue before the suture anchor is implanted. For safety and sterility reasons, it may also be desirable to fix the driver mechanisms in a fully retracted position so that they are not accidentally advanced prior to the surgical procedure, such as during packaging or shipping, or after the surgical procedure has been completed.

As shown in FIG. 24B, the toggle mechanism 366 includes at least one toggle channel 368, 370 in the housing and at least one detent 372, 374 positioned along and opening up to the channel 368, 370. The detents 372, 374 define the positions in which the surgeon may fix a driver mechanism. In one embodiment, the toggle mechanism 366 includes three detents 372, 374, one defining a fully retracted position, a fully extended position and an intermediate position lying therebetween. To lock the driver mechanism in one of the preset positions, pin 376, 378, connected to the fin 344, 346, is received in the toggle 372, 374 of the desired position. To achieve this, a slit 380, 382 is provided in the fin 344, 346 which allows the pin 376, 378 to essentially be squeezed together and pressed downward from a detent and into toggle channel 368, 370. The toggle mechanism 366 may be provided in one or both of the driver mechanisms 312, 314.

Figure 33:
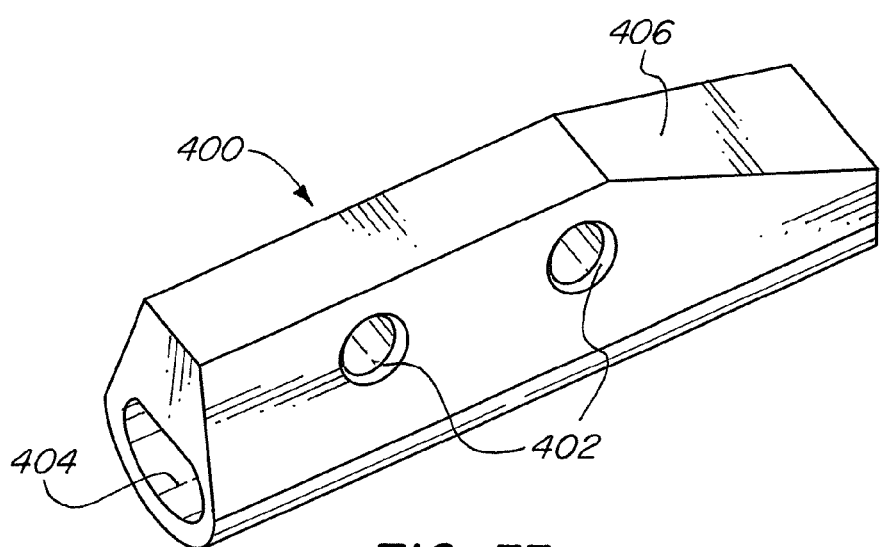
FIG. 33 is a projected view of an embodiment of a suture anchor of the present invention.

One embodiment of a suture anchor 400 of the present invention is shown in FIG. 33. The anchor 400 includes at least two eyelets 402 and a longitudinal channel 404 for receiving the distal end of a delivery needle 332, 334. The channel 404 and at least a distal portion of the needle 332, 334 may be non-circular in cross section to prevent the anchor 400 from rotating on the needle. The anchor 400 may also be provided with a tapered leading edge 406 to facilitate in implantation.

Figure 35:
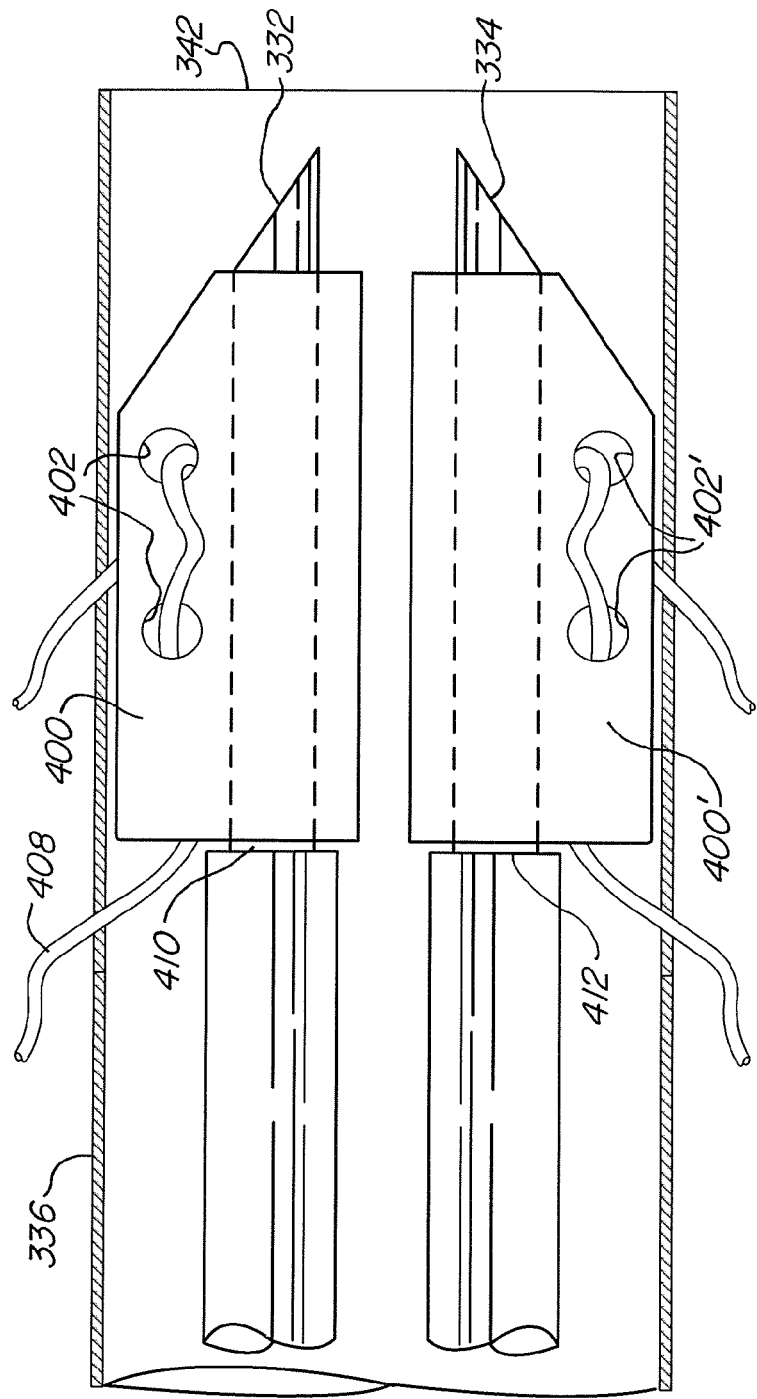
FIG. 35 is a top partial sectional view of an embodiment of the delivery device depicted in FIG. 22, showing two suture anchors.
Figure 36:
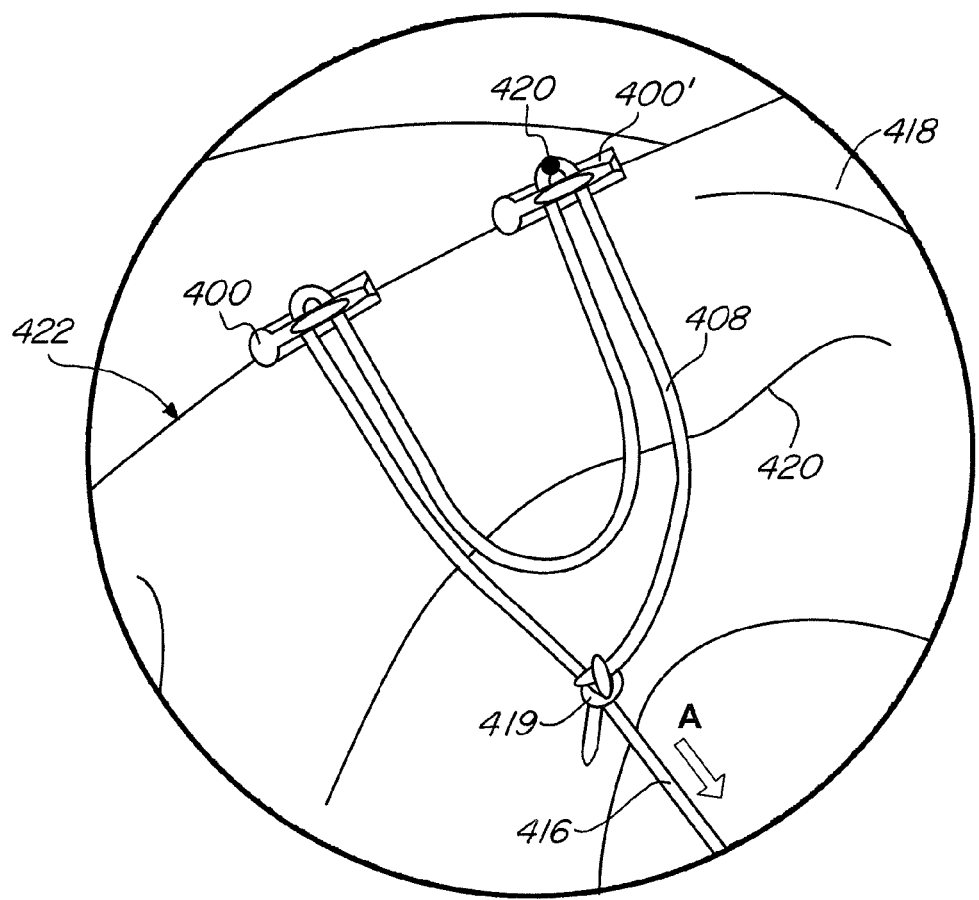
FIG. 36 is a view of an embodiment of the suture holding system of the present invention having two suture anchors being used to repair a tear in soft tissue.
Figure 37:
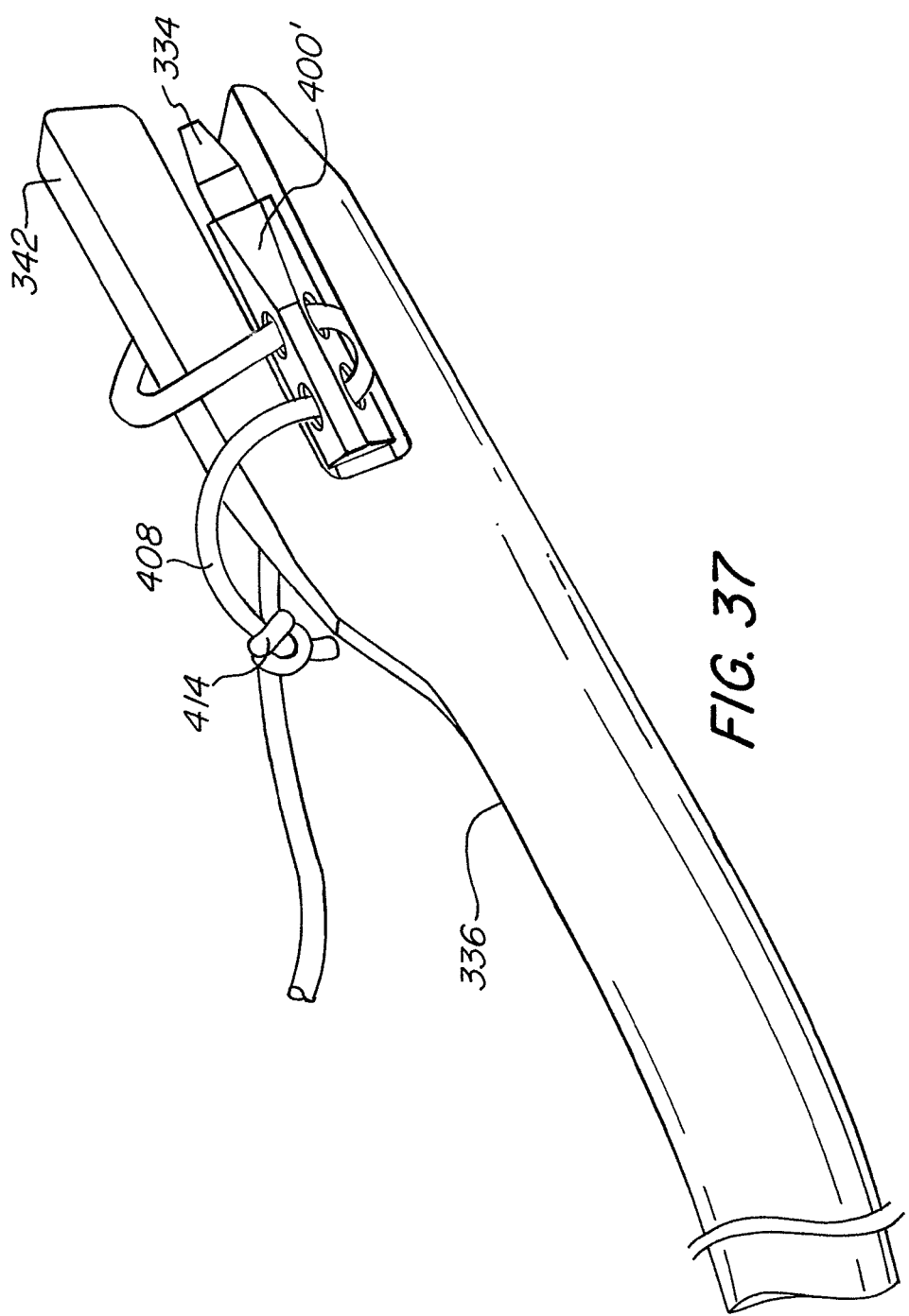
FIG. 37 is a projected partial view of an embodiment of the suture holding system, including an embodiment of the delivery device depicted in FIG. 22.

In operation, first and second anchors 400, 400', with a suture 408 threaded therebetween, are loaded on to needles 332, 334 engaging shoulders 410, 412 as shown in FIG. 35. In one embodiment, a single strand of suture 408 is threaded through the first anchor 400 and then through the second anchor 400', with a locking slip-knot 414 connecting the two ends of suture. The free end 416 of suture 408 may be pulled in the direction of arrow A to tighten the loop of suture passing through the tissue 418 to close tear 420. Any other suitable knot may also be used. The suture, loaded on the anchors, may then pass out of the distal end 342 of the cannula 336 through the slots therein, as shown in FIG. 37.

To implant the anchors 400, 400', the surgeon positions the delivery device 300 at the area of interest, for example, near a tear in a meniscus. The surgeon then engages the first driver mechanism 312, for example, by placing his/her thumb on the first pusher 316, and advances the first driver mechanism 312 in a distal direction thereby advancing first needle 332 carrying the first implant 400. As the surgeon advances the first driver mechanism 312, the first needle 332, which may have a pointed distal end, then enters tissue 418, crosses the tear 420, and continues until the needle 332 exits the surface 422 of the tissue. In the interim of this process, the surgeon may use the toggle mechanism 366 to fix the driver mechanism 312 at an intermediate position to, for example, determine if the needle is properly positioned across the tear. If the surgeon does not like the positioning, he may retract the needle and correct the placement.

Once the driver mechanism reaches its fully extended position, the first anchor 400 will be disengaged from the first needle. The surgeon may also fix the first needle 312 in the fully extended position via the toggle mechanism 366 while he/she, for example, disengages the first anchor 400 or adjusts the suture 408. As described above, until the first driver mechanism 312 reaches the fully extended position, the control mechanism 348 prevents the second driver mechanism 314 from advancing in a distal direction. The same procedure is used to implant the second suture anchor 400'. Once both anchors 400, 400' are implanted, the surgeon may then pull free end 416 of the suture in the direction of arrow A to tighten the length of suture between the implants and close the tear 420.

Additionally, in one embodiment, a stop knot 420, which may be a single overhand knot, may also be provided in the length of suture between the eyelets 402' of the second suture anchor 400'. This stop knot 420 aids in tightening of the anchor construct. Without the knot, tightening of the construct can be difficult because of the multiple lengths of suture that pass through the tissue 418, which can cause the suture to get caught up and not slide well. With the stop knot 420, the length of the suture portion between the slip-knot 414 and stop knot 420 is fixed and not adjustable.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A suture anchor delivery system, comprising:
   a housing having a distal end and a proximal end;
   a first longitudinal channel and a second longitudinal channel disposed within the housing, the first longitudinal channel and the second longitudinal channel being adjacent to one another and open to a top surface of the housing;
   a bore disposed within the housing and extending in a lateral direction between the first longitudinal channel and the second longitudinal channel;
   a first driver and a second driver, each movable in a distal direction toward said distal end of said housing, from a respective fully retracted position to a respective fully extended position, the first driver being disposed in the first longitudinal channel and the second driver being disposed in the second longitudinal channel;
   a first delivery needle and a second delivery needle, said first delivery needle connected at a proximal end to said first driver and said second delivery needle connected at a proximal end to said second driver;
   a control operable to prevent said second driver from being moved in the distal direction from its respective fully retracted position toward its respective fully extended position until said first driver is moved in the distal direction to its respective fully extended position;
   wherein said control includes a first pin, the first pin having a pin body slidable in the lateral direction within the bore between a locked position and an unlocked position, wherein said pin body is in the locked position until the first driver is moved in the distal direction to its respective fully extended position, and is in the unlocked position after the first driver is moved in the distal direction to its respective fully extended position.

2. The suture anchor delivery system of claim 1, further comprising:
   a toggle assembly operable to fix at least one of said first driver and second driver in at least one longitudinal position.

3. The suture anchor delivery system of claim 2, wherein said toggle assembly comprises:
   a second pin connected at a first end to at least one of said first driver and second driver and;
   an axial channel disposed in said housing, a second end of said second pin slidably disposed within said axial channel; and
   at least one detent open to said axial channel and adapted to receive said second pin.

4. The suture anchor delivery system of claim 3, wherein said toggle assembly comprises at least three detents spaced longitudinally along said channel.

5. The suture anchor delivery system of claim 2, wherein said toggle assembly is operable to fix a least one of said first driver and second driver in at least one of said fully extended position, said fully retracted position, and an intermediate position spaced longitudinally between said fully retracted and fully extended positions.

6. The suture anchor delivery system of claim 2, wherein said toggle assembly is operable to fix said first driver and said second driver each in at least one longitudinal position.

7. The suture anchor delivery system of claim 1, further comprising a first suture anchor and a second suture anchor.

8. The suture anchor delivery system of claim 7, wherein each of said first and second delivery needles includes a shoulder for engaging said first suture anchor and said second suture anchor, respectively.

9. The suture anchor delivery system of claim 8, wherein a distal portion of each of said first and second delivery needles is non-circular in cross-section.

10. The suture anchor delivery system of claim 9, wherein a longitudinal bore in said first and second suture anchors is non-circular.

11. The suture anchor delivery system of claim 7, wherein said first suture anchor has a longitudinal bore therein for receiving said first delivery needle therein and said second suture anchor has a longitudinal bore therein for receiving said second delivery needle therein.

12. The suture anchor delivery system of claim 1, wherein the pin body extends between a first end and a second end;
   wherein in the locked position, the first end of the pin body extends into the second longitudinal channel at a position distal of the second driver, preventing the second driver from being moved in the distal direction from its respective fully retracted position toward its respective fully extended position; and
   wherein the control further includes a spring that biases the pin body toward the unlocked position.

13. The suture anchor delivery system of claim 12, wherein in the unlocked position, the first end of the pin body is positioned completely within the bore, permitting the second driver to be moved in the distal direction from its respective fully retracted position toward its respective fully extended position, and the second end of the pin body extends into the first longitudinal channel.

14. The suture anchor delivery system of claim 13, wherein the control is configured to permit the first drive to be moved in a proximal direction toward the proximal end of the housing, from its respective fully extended position to its respective fully retracted position.

15. The suture anchor delivery system of claim 1, wherein the first longitudinal channel extends along a first longitudinal axis, the second longitudinal channel extends along a second longitudinal axis, the bore extends along a third longitudinal axis, the first and second longitudinal axes extend parallel relative to one another, and the third longitudinal axis extends laterally relative to the first and second longitudinal axes.

* * * * *